US008329395B2

(12) United States Patent
Goese et al.

(10) Patent No.: US 8,329,395 B2
(45) Date of Patent: Dec. 11, 2012

(54) THIAMIN PRODUCTION BY FERMENTATION

(75) Inventors: Markus G. Goese, Basel (CH); John B. Perkins, Reinach (CH); Ghislain Schyns, Aesch (CH)

(73) Assignee: DSM IP Assets B.V., Te Heerlen (NL)

( * ) Notice: Subject to any disclaimer, the term of this patent is extended or adjusted under 35 U.S.C. 154(b) by 175 days.

(21) Appl. No.: 12/380,610

(22) Filed: Mar. 2, 2009

(65) Prior Publication Data

US 2009/0233296 A1     Sep. 17, 2009

Related U.S. Application Data

(63) Continuation of application No. 10/559,307, filed as application No. PCT/CH2004/000321 on May 27, 2004, now abandoned.

(60) Provisional application No. 60/475,323, filed on Jun. 2, 2003.

(51) Int. Cl.
    *C12Q 1/68* (2006.01)
    *C12N 1/21* (2006.01)
    *C12P 17/16* (2006.01)
    *C07H 21/04* (2006.01)

(52) U.S. Cl. .................... 435/6; 435/525.5; 435/252.31; 435/118; 536/23.1

(58) Field of Classification Search ............. 435/252.31, 435/122, 252.9, 6, 118, 252.5; 536/23.1
    See application file for complete search history.

(56) References Cited

FOREIGN PATENT DOCUMENTS

EP     0 417 953 A1     3/1991

OTHER PUBLICATIONS

Petersen and Downs, "Identification and Characterization of an Operon in *Salmonella typhimurium* Involved in Thiamine Biosynthesis," J. Bact., vol. 179, No. 15, pp. 4894-4900 (1997).
Kunst, F. et al., "The Complete Genome Sequence of the Gram-positive Bacterium *Bacillus subtilis*," Nature, vol. 390, pp. 249-256 (1997).
Begley, T.P. et al., "Thiamin Biosynthesis in Prokaryotes," Arch. Microbiol., vol. 171, pp. 293-300 (1999).
Kawasaki, T., "Thiamine Phosphate Pyrophosphorylase," Methods in Enzymology, vol. 62, pp. 69-73 (1979).
Foulger et al. Database DDBJ/EMBL/Genbank. Accession No. Y13937, [online]. [retrieved on Apr. 4, 2012] Retrieved from the Internet: <URL: http://www.ncbi.nlm.nih.gov/nucleotide/2337793/>.
Rodionov, D. A. Comparative Genomics of Thiamin Biosynthesis in Procaryotes. The Journal of Biological Chemistry, vol. 277, No. 50 (Dec. 13, 2002), pp. 48949-48959.

*Primary Examiner* — Chih-Min Kam
(74) *Attorney, Agent, or Firm* — Bryan Cave LLP

(57) ABSTRACT

The present invention provides a method for producing thiamin products using a microorganism containing a mutation that causes it to overproduce and release thiamin products into the medium. Biologically pure cultures of the microorganisms and isolated polynucleotides containing the mutations are also provided. In addition, methods for detecting a pathogenic microorganism in a clinical sample, assays for identifying an antibiotic, as well as, antibiotics identified by such assays are provided.

6 Claims, 3 Drawing Sheets

A.

B.

Strain TH95: Thiamin-prototroph

Strain TH403: Thiamin-auxotroph

Strain TH404: Thiamin-prototroph

THIAMIN PRODUCTION BY FERMENTATION

This application claims priority to and is a continuation of U.S. patent application Ser. No. 10/559,307, filed Dec. 2, 2005, now abandoned. The '307 application is the National Stage of International Application No. PCT/CH2004/000321, filed May 27, 2004, which claims priority to U.S. provisional application No. 60/475,323, filed Jun. 2, 2003.

The present invention relates to methods for producing thiamin products. More particularly, the present invention relates to methods for producing thiamin products using a microorganism containing a mutation that causes it to overproduce and release thiamin products into the medium. Biologically pure cultures of the microorganisms and isolated polynucleotides containing the mutations are also provided. In addition, methods for detecting a pathogenic microorganism in a clinical sample, assays for identifying an antibiotic, as well as, antibiotics identified using such assays are provided.

Thiamin, also known as vitamin B1, is a member of the water-soluble B-complex of vitamins and is a nutritional requirement for mammals. The pyrophosphate form of thiamin acts in vivo as the coenzyme in many carbohydrate and amino acid metabolic pathways, like for example those catabolized by pyruvate dehydrogenase, pyruvate oxidase or transketolase. It is important to note that unlike other vitamin biosynthetic pathways (e.g. riboflavin and biotin), thiamin is not part of the de novo pathway, but is actually part of the salvage pathway.

Most enzymatic steps and intermediates in thiamin biosynthesis have been studied in *E. coli* and to a lesser extent in *Salmonella typhimurium* and *Rhizobium* (for reviews, see Brown and Williamson (1987) pp. 528-532, In F. C. Neidhardt et al. (ed.) *Escherichia coli* and *Salmonella typhimurium*: Cellular and Molecular Biology, vol. 1. American Society for Microbiology, Washington, D.C.; White and Spenser (1996) pp. 680-686, In F. C. Neidhardt et al. (ed.) *Escherichia coli* and *Salmonella typhimurium*: Cellular and Molecular Biology, vol. 2. American Society for Microbiology, Washington, D.C.; Begley et al. (1999) *Arch. Microbiol*. 171: 293-300). The *E. coli* genes encoding the steps in the thiamin pathway are located at four distinct sites on the chromosome: a thiCEFSGH operon at 90–; a thiMD operon at 46–, individual thiJ and thiL genes are clustered in the 9.5" vicinity and thiK at 25". All of these genes have been cloned and sequenced and many of the enzymes encoded by these genes have been overproduced in *E. coli* and their enzymatic activities determined.

The pyrimidine moiety, 4-amino-5-hydroxymethyl-2-methylpyrimidine phosphate (HMP-P), is derived from 5-aminoimidazole ribotide (AIR), an intermediate in the de novo purine biosynthetic pathway. In Gram-negative bacteria, conversion of AIR to HMP-P is catalyzed by the thiC gene product. HMP-P is then phosphorylated to HMP-PP by ThiD kinase prior to coupling with the thiazole unit.

The thiazole moiety, 5-(2-hydroxyethyl)-4-methylthiazole phosphate (HET-P), is derived from L-tyrosine and 1-deoxy-D-xylulose phosphate (DXP); the sulfur atom is most likely derived from L-cysteine. This reaction requires expression of at least five genes thiF, thiS, thiG, thiH and thiI.

Coupling of HMP-PP and HET-P is catalyzed by thiamin phosphate pyrophosphorylase encoded by thiE, resulting in thiamin monophosphate (TMP). TMP is then phosphorylated to form thiamin pyrophosphate (TPP) by the action of thiamin monophosphate kinase, encoded by thiL. Because thiamin is not part of the de novo pathway, *E. coli* requires a salvage enzyme, thiamin kinase, encoded by thiK to convert exogenous thiamin into TMP.

Synthesis of thiamin in *B. subtilis* appears to utilize the same enzymes and intermediates as found in *E. coli* (see, e.g., Perkins and Pero (2001) pp. 271-286, In Sonenshein et al, (ed.) *Bacillus subtilis* and its relatives: from genes to cells, American Society for Microbiology, Washington, D.C.). However there are important differences. The traditional gene names are different in *E. coli* and *B. subtilis*. First, the HMP biosynthesis enzyme ThiC, thiamin-phosphate pyro phosphate ThiE, and hydroxyethylthiazole kinase ThiM from *E. coli* have their counterparts named ThiA, ThiC, and ThiK, respectively. Second, the known *B. subtilis* thiamin biosynthetic genes are organized differently, as three clusters: the thiA locus consisting of only the thiA gene, the thiB locus consisting of genes thiOSFGD1, and the thiC locus consisting of thiK and thiC genes. Third, at least one enzymatic step in thiazole biosynthesis is different. The *B. subtilis* genome does not contain a thiH ortholog. Instead thiO (yjbR in the thiB locus) is predicted to encode an oxidase activity involved in thiazole biosynthesis. This gene is not present in the *E. coli* genome, nor does it show amino acid homology to ThiH. It is homologous to one of the genes (thiO) associated with thi genes from *Rhizobium etli*. Fourth, two orthologs of *E. coli* thiD have been found in *B. subtilis*, yjbV (thiD1) and ywdB (thiD2), which could encode the biosynthetic and salvage HMP kinases. Finally, the thiC locus contains an unknown gene, ywbI that displays strong similarity to the lysR family of transcriptional regulators.

The present invention provides a microorganism selected from the group consisting of Bacillaceae, Lactobacillaceae, Streptococcaceae, Corynebacteriaceae and Brevibacteriaceae, wherein the microorganism contains a mutation that deregulates thiamin production and causes thiamin products to be released from the cell.

"Thiamin products" means thiamin, thiamin monophosphate (TMP) and/or thiamin pyrophosphate (TPP), either alone or in any combination.

It is understood that a microorganism as used for the present invention means a "biologically pure culture" of said microorganism, i.e., a microorganism that is separated from constituents, cellular and otherwise, in which the microorganism is normally associated with in nature.

The following materials have been deposited with the American Type Culture Collection (ATCC), P. O. Box 1549, Manassas, Va. 20108 USA on May 12, 2003, and with the Deutsche Sammlung von Mikroorganismen und Zellkulturen (DSMZ), Mascheroder Weg 1B, D-38124 Braunschweig, Germany on Apr. 5, 2004, respectively, with the corresponding accession numbers as indicated below, in accordance with the stipulations of the Budapest Treaty: *Bacillus subtilis* TH95 (ATCC PTA-5221), *Bacillus subtilis* TH101 (ATCC PTA-5222), *Bacillus subtilis* TH115 (ATCC PTA-5223), *Bacillus subtilis* TH116 (ATCC PTA-5224), *Bacillus subtilis* TH404 (DSM 16333), and *Baillus subtilis* TH405 (DSM 16334).

"Mutation" is used interchangeably herein with modification to mean a change in the wild-type DNA sequence of a microorganism, such as a bacterium, that conveys a phenotypic change to the microorganism compared to the wild type microorganism, e.g. that allows an increase or decrease of thiamin or a thiamin product either in the cell or out of the cell by any mechanism. The mutation may be caused in a variety of ways including one or more frame shifts, substitutions, insertions and/or deletions, including nonsense mutations (amber (UAG), ocher (T/UAA) and opal (T/UGA)). The deletion may be of a single nucleotide or more, including deletion of the entire gene.

"Amino acid substitution" means a one-for-one amino acid replacement. Such substitutions are conservative in nature when the substituted amino acid has similar structural and/or chemical properties. Examples of conservative replacements include substitution of a leucine with an isoleucine or valine, an aspartate with a glutamate, or a threonine with a serine. Non-conservative substitutions within the scope of the present invention include replacement of amino acids having aliphatic side chains with those that have aromatic side chains, such as replacement of leucine with phenylalanine.

Amino acid "insertions" or "deletions" mean changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the sequence using recombinant DNA techniques.

"Deregulates" or "deregulation" means an alteration or modification of the expression of a gene that encodes an enzyme/protein in a biosynthetic pathway, such that the level or activity of said enzyme/protein is altered or modified, which results in, but is not limited to, an increase in the production of a thiamin product or the release of thiamin products out of the cell, by e.g., secretion, efflux, and the like. Alterations or modifications of gene expression can occur by changes in the DNA sequence of the gene itself or regions outside of the gene, including non-protein encoding DNA regions. "Deregulates" or "deregulation" can also mean any perturbation of the intracellular levels of a metabolite that alters the expression of a biosynthetic gene of the cell, such that an increase in the production or the release of thiamin products occurs.

In one embodiment, the mutation that deregulates thiamin production in a microorganism as defined above is selected from the group consisting of ΔthiL, tx1, tx26 and combinations thereof. Such a mutation includes ΔthiL combined with tx1, ΔthiL combined with tx26, tx1 combined with tx26, and ΔthiL combined with both tx1 and tx26. Preferred is a microorganism comprising all three mutations ΔthiL, tx1 and tx26.

In a preferred embodiment, the microorganism is selected from the group consisting of *Bacillus, Lactobacillus, Lactococcus, Corynebacterium*, and *Brevibacterium*. More preferably, the microorganism is selected from the genus *Bacillus*, most preferably it is a *B. subtilis* cell.

In one embodiment, the microorganism containing the mutation as defined above is *B. subtilis* TH95.

In one embodiment, the present invention provides a microorganism as defined above containing a mutation which is selected from the group consisting of ΔthiL, tx1, tx26 and combinations thereof further comprising a DNA cassette containing at least one copy of a polynucleotide sequence that encodes a thiA gene product, which polynucleotide sequence is operatively controlled by a strong constitutive promoter. A preferred microorganism is *B. subtilis* TH116.

In a further embodiment, the present invention provides a microorganism as defined above containing a mutation which is selected from the group consisting of ΔthiL, tx1, tx26 and combinations thereof further comprising a DNA cassette containing at least one copy of a polynucleotide sequence that encodes gene products from a thiKC operon, which polynucleotide sequence is operatively controlled by a strong constitutive promoter. A preferred microorganism is *B. subtilis* TH115.

In a further embodiment, the present invention provides a microorganism as defined above containing a mutation which is selected from the group consisting of ΔthiL, tx1, tx26 and combinations thereof further comprising a DNA cassette containing a polynucleotide sequence that encodes gene products of a tenAl-thiOSGFD operon, which polynucleotide sequence is operatively controlled by a strong constitutive promoter. A preferred microorganism is *B. subtilis* TH404.

In a further embodiment, the present invention provides a microorganism as defined above containing a mutation which is selected from the group consisting of ΔthiL, tx1, tx26 and combinations thereof further comprising (a) a DNA cassette containing a polynucleotide sequence that encodes gene products of a tenAl-thiOSGFD operon and (b) a DNA cassette containing at least one copy of a polynucleotide sequence that encodes a thiA gene product, which polynucleotide sequences are operatively controlled by a strong constitutive promoter. A preferred microorganism is *B. subtilis* TH405.

In the present invention, "DNA cassette" means a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. DNA fragments can also be inserted into the vector DNA without restriction enzymes by the use of topoisomerase bound at the ends of linearized vector DNA; this is especially useful for direct cloning of PCR-prepared DNA fragments. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can be readily introduced into a suitable host cell. A plasmid often contains coding DNA and promoter DNA and has one or more restriction sites suitable for inserting foreign DNA. "Coding DNA" is a DNA sequence that encodes a particular amino acid sequence for a particular protein or enzyme. The DNA cassette may, in addition to the specific nucleotide sequence, contain additional transcription control elements including enhancers and promoters for controlling transcription of the specific nucleotide sequence. "Promoter DNA" is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include those specifically described in the Examples, as well as, pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), pCR2.1Topo (Invitrogen, San Diego, Calif.), pXLTopo (Invitrogen, San Diego, Calif.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The DNA cassette may contain one or more copies of the coding DNA such as for example from 1-50 copies of the sequence, preferably from 1-25 copies, such as from 1-5, 1-10, 1-15 and 1-20 copies. The sequences may be arranged in any order, including for example, tandemly, i.e., in a head-to-tail arrangement.

"Operatively controlled" means that the transcription of the coding DNA is controlled or mediated by e.g., a promoter or transcription enhancer. Such promoters or transcription enhancers may be adjacent to the coding DNA or may be located upstream or downstream from the coding DNA.

A "strong constitutive promoter" is one which causes mRNAs to be initiated at high frequency compared to a native host cell. Strong constitutive promoters are well known and an appropriate one may be selected according to the specific sequence to be controlled in the host cell. Examples of such strong constitutive promoters from Gram-positive microorganisms include, but are not limited to, SP01-26, SP01-15, veg, pyc (pyruvate carboxylase promoter), and amyE. Examples of promoters from Gram-negative microorganisms include, but are not limited to, tac, tet, trp-tet, lpp, lac, lpp-lac, lacIq, T7, T5, T3, gal, trc, ara, SP6, $\lambda$-$P_R$, and $\lambda$-$P_L$.

In another aspect, the present invention provides a microorganism as defined above containing a mutation which is selected from the group consisting of $\Delta$thiL, tx1, tx26 and combinations thereof further comprising (a) a first mutation that deregulates expression of a purine operon of *B. subtilis* and (b) a second mutation that blocks conversion of 5-aminoimidazole ribotide (AIR) to carboxyaminoimidazole ribotide (CAIR). In a preferred embodiment, the first mutation comprises a mutation within the leader region of the pur operon and the second mutation comprises a mutation within the purE gene encoding phosphoribosylaminoimidazole carboxylase I. More preferably, the microorganism is *B. subtilis* TH101.

The term "blocks conversion" means that the mutation prevents the cellular machinery from converting AIR to CAIR. In the present invention, the conversion of AIR to CAIR is preferably completely blocked; but blockage of the conversion of greater than 75%, such as greater than 85-90% is also acceptable.

In one embodiment, the present invention is a method or a process for producing thiamin products. This method comprises culturing, in a suitable medium, a microorganism as defined above containing a mutation which is selected from the group consisting of $\Delta$thiL, tx1, tx26 and combinations thereof that causes it to overproduce thiamin products and to release them into the medium. The thiamin products are then recovered from the medium.

"Overproduce" means that the microorganism(s) of the present invention or the microorganism(s) used in the methods of the present invention is/are engineered to produce one or more thiamin products in excess of what the native microorganism would produce as measured by any of the methods set forth in the examples. A substantial amount of such thiamin products are released into the culture media, by e.g., secretion or efflux. As used herein, a "substantial amount" means more than 75%, preferably more than 85%, such as between 90-95% of the thiamin products produced by the cell are released into the media.

"Recovering" when used in conjunction with "thiamin products" means separating the thiamin products from the medium and/or isolating the recovered thiamin products into pure or semi-pure form. Any conventional method for recovering thiamin products from, e.g., a fermentation broth may be used in the present invention. Recovering can also mean isolation of thiamin products by use of HPLC.

In one aspect, the method as defined above further comprises culturing said microorganism in the presence of thiamin precursors. Preferred precursors are selected from the group consisting of 4-amino-5-hydroxymethyl-2-methylpyrimidine (HMP), 5-(2-hydroxyethyl)-4-methylthiazole (HET) and a combination thereof.

If in the method for producing thiamin products as defined above said microorganism further comprises a mutation that deregulates the expression of a purine operon of *B. subtilis* as described above, it is another aspect of the present invention to provide a method wherein said microorganism is cultured in the presence of a thiamin precursor and a purine source. In a preferred embodiment, the thiamin precursor is HET and the purine source is xanthine.

In another aspect, the method as defined above further comprises culturing said microorganism in the presence of a precursor of a HET pathway. A "precursor of a HET pathway" means a carbon-containing compound that is utilized to make 5-(2-hydroxyethyl)-4-methylthiazole (HET). Such precursors are preferably selected from the group consisting of glycine, cysteine, isoleucine, threonine, and combinations thereof.

In another aspect, the method as defined above further comprises culturing said microorganism in the presence of a precursor of a HMP pathway or derivative of HMP. A "precursor of a HMP pathway" means a carbon-containing compound that is utilized to make 4-amino-5-hydroxymethyl-2-methylpyrimidine (HMP). Non-limiting examples of such a precursor include 5-aminoimidazole ribotide (AIR). A "derivative of HMP" means any chemically modified variant of HMP that functions in the same manner as 4-amino-2-methyl-5-pyrimidinemethaneamine (Grewe Diamine).

Thus, the present invention is directed to a method for producing thiamin products comprising (a) culturing, in a suitable medium, a microorganism selected from the group consisting of Bacillaceae, Lactobacillaceae, Streptococcaceae, Corynebacteriaceae and Brevibacteriaceae, the microorganism containing a mutation that causes it to overproduce thiamin products into the medium; and (b) recovering the thiamin products.

In one embodiment, the invention is directed to a method as defined above wherein the microorganism contains a mutation, said mutation comprising $\Delta$thiL, tx1, and tx26.

In one embodiment, the invention is directed to a method as defined above wherein the microorganism further comprises a DNA cassette containing at least one copy of a polynucleotide sequence that encodes a thiA gene product, which polynucleotide sequence is operatively controlled by a strong constitutive promoter.

In one embodiment, the invention is directed to a method as defined above wherein the microorganism further comprises a mutation that deregulates expression of a purine operon of *B. subtilis* and a mutation that blocks conversion of 5-aminoimidazole ribotide (AIR) to carboxyaminoimidazole ribotide (CAIR).

In one embodiment, the invention is directed to a method as defined above wherein the microorganism further comprises a DNA cassette containing at least one copy of a polynucleotide sequence that encodes gene products from a thiKC operon, which polynucleotide sequence is operatively controlled by a strong constitutive promoter.

In one embodiment, the invention is directed to a method as defined above wherein the microorganism further comprises a DNA cassette containing at least one copy of a polynucleotide sequence that encodes gene products of a tenAl-thiOS-GFD operon, which polynucleotide sequence is operatively controlled by a strong constitutive promoter.

In one embodiment, the invention is directed to a method as defined above wherein the microorganism further comprises (a) a DNA cassette containing at least one copy of a polynucleotide sequence that encodes gene products of a tenAlthiOSGFD operon and (b) a DNA cassette containing at least one copy of a polynucleotide sequence that encodes a thiA gene product, which polynucleotide sequence is operatively controlled by a strong constitutive promoter.

In another embodiment, the invention is an isolated polynucleotide sequence comprising a tx1 mutation. Such mutation is useful for the construction of a recombinant microorganism wherein the production of thiamin is increased, e.g. a microorganism selected from the group consisting of Bacillaceae, Lactobacillaceae, Streptococcaceae, Corynebacteriaceae and Brevibacteriaceae, containing a mutation that deregulates thiamin production and causes thiamin products to be released into the culture medium. Preferred is a mutation which results in a leucine to phenylalanine substitution at amino acid residue 116 (see SEQ ID NO: 31 for a copy of the amino acid sequence having the Leu to Phe substitution on position 116 in comparison to the wild type YloS sequence ID NO: 32).

As used herein, an "isolated" polynucleotide (e.g., an RNA, DNA or a mixed polymer) or polypeptide means substantially separated from components that accompany it in its natural state. In the case of polynucleotides, "isolated" means separated from other cellular components which naturally accompany a native sequence, e.g., ribosomes, polymerases, many other genome sequences and proteins. The term embraces a polynucleotide that has been removed from its naturally occurring environment, and includes recombinant or cloned DNA isolates and chemically synthesized analogs or analogs biologically synthesized by heterologous systems. With respect to polypeptides, the term "isolated" means a protein or a polypeptide that has been separated from components that accompany it in its natural state. A monomeric protein is isolated when at least about 60 to 75% of a sample exhibits a single polypeptide sequence. An isolated protein will typically comprise about 60 to 90% w/w of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, using HPLC or other means well known in the art may provide higher resolution for purification.

In one embodiment, the isolated polynucleotide sequence as defined above is SEQ ID NO: 30 or a polynucleotide sequence that hybridizes to SEQ ID NO: 30 under stringent conditions and, when present in a microorganism, causes deregulation of thiamin production.

Nucleic acids which hybridize under "stringent conditions" to the polynucleotide sequences identified herein and that retain the same function, i.e., when introduced into an appropriate cell cause a deregulation of thiamin production, are within the scope of the present invention. "Stringent conditions" are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. For the purposes of this disclosure, suitable "stringent conditions" for such hybridizations are those which include hybridization in a buffer of 40% formamide, 1M NaCl, 1% sodium dodecyl sulfate (SDS) at 37° C., and at least one wash in 0.2×SSC at a temperature of at least about 50° C., usually about 55° C. to about 60° C., for 20 minutes, or equivalent conditions. A positive hybridization is at least twice above the level of background. Those of ordinary skill will readily recognize that alternative hybridization and wash conditions can be utilized to provide conditions of similar stringency.

The phrase "nucleic acid sequence" means a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed base and/or deoxyinosine residues (Batzer et al., *Nucleic Acid Res.* 19:5081 (1991); Ohtsuka et al., *J. Biol. Chem.* 260:2605-2608 (1985); Cassol et al., 1992; Rossolini et al., *Mol. Cell. Probes* 8:91-98 (1994)).

In another embodiment, the invention is two unlinked mutations: an isolated polynucleotide sequence comprising a first mutation tx26-1 and a second mutation tx26-2 wherein the presence of both mutations in a thiamin-producing microorganism causes a deregulation of thiamin production. The first mutation, tx26-1, exhibits a 70% linkage to ΔyufR::Tn917 (BGSC#1A642) and the second mutation, tx26-2, exhibits a 59% linkage to ΩmotA::Tn917 (BGSC#1A631). Thus, the present invention is directed to an isolated polynucleotide sequence comprising a first mutation with 70% linkage to ΔyufR::Tn917 (tx26-1) and a second mutation with 59% linkage to ΩmotA::Tn917 (tx26-2) wherein the presence of both of the mutations in a thiamin-producing microorganism causes a deregulation of thiamin production.

Preferably, the tx26-1 mutation is encoded by a polynucleotide sequence which is SEQ ID NO: 33 or a polynucleotide sequence that hybridizes to SEQ ID NO: 33 under stringent conditions and, when present in a microorganism in combination with a tx26-2 mutation, causes a deregulation of thiamin production.

Preferably, the tx26-2 mutation is encoded by a polynucleotide sequence which is SEQ ID NO: 36 or a polynucleotide sequence that hybridizes to SEQ ID NO: 36 under stringent conditions and, when present in a microorganism in combination with a tx26-1 mutation, causes a deregulation of thiamin production.

Furthermore, a DNA cassette comprising one or more polynucleotides as defined above, i.e., (a) an isolated polynucleotide sequence comprising a first mutation tx26-1 and a second mutation tx26-2 or (b) an isolated polynucleotide sequence comprising a tx1 mutation, as well as a microorganism containing such DNA cassette is provided by the present invention.

A further embodiment is a method for detecting a pathogenic microorganism in a clinical sample from a patient. This method comprises determining whether a Gram-positive (Gram$^+$) microorganism is present in the sample, determining whether the microorganism contains a yloS ortholog, and determining whether the microorganism contains a thiL ortholog, wherein the presence of a yloS ortholog and the absence of a thiL ortholog in a Gram$^+$ microorganism indicates that the microorganism is pathogenic.

A "clinical sample" means any assayable specimen taken from a patient, which is a mammal, preferably a human or a feed animal. An assayable specimen may be selected from blood, urine, fecal, sputum, tissue or other biological sources from which microorganisms, if present, may be identified and characterized as disclosed in the Examples.

The microorganisms that are detected in a clinical sample from a patient as defined above are preferably selected from the group consisting of *Listeria, Staphylococcus, Clostridium, Enterococcus*, and *Streptococcus*, most preferably from *Listeria monocytogenes, Staphylococcus aureus, Staphylococcus epidermidis, Clostridium tetani, Clostridium perfringens, Enterococcus* sp., *Streptococcus agalactiae, Streptococcus pyogenes*, and *Streptococcus pneumoniae*.

The YloS protein is a valuable target for identifying bacteriocidal compounds because many Gram$^+$ bacteria that contain only a yloS ortholog and not a thiL ortholog are known pathogens. Accordingly, the present invention also provides a screening assay (or method) for identifying modulators, i.e., candidate or test compounds or agents (e.g., peptides, peptidomimetics, small molecules or other drugs) that bind to YloS, or have a stimulatory or inhibitory effect on, for example, yloS expression or YloS activity.

In one embodiment, an assay is provided for identifying an antibiotic comprising (a) contacting an assay composition comprising a YloS protein with a test compound and (b) determining whether the test compound inhibits YloS protein activity, wherein the compound is identified as an antibiotic based on the compound's ability to inhibit the activity of the YloS protein activity. Preferably, the assay comprises a purified YloS protein, a partially purified YloS protein, a crude cell extract from a cell producing YloS protein, or the YloS protein is encoded by a polynucleotide derived from a pathogenic microorganism selected from the group consisting of *Listeria, Staphylococcus, Clostridium, Enterococcus*, and *Streptococcus*. Such pathogenic microorganisms include, but are not limited to, *Listeria monocytogenes, Staphylococcus aureus, Staphylococcus epidermidis, Clostridium tetani, Clostridium perfringens, Enterococcus* sp., *Streptococcus agalactiae, Streptococcus pyogenes*, and *Streptococcus pneumoniae*.

An "assay composition" in reference to the assays for identifying an antibiotic means the components in combination that are required to conduct such an assay. Such an assay composition requires at a minimum the YloS protein or biologically active portion thereof and the test compound, i.e., the peptide, peptidomimetic, small molecule or other drug to be tested.

As used herein, "YloS activity" means any detectable or measurable activity of the YloS protein, i.e., the protein encoded by the yloS gene. In the present invention, YloS activity is at least one of the following: (1) modulation of at least one step in the YloS biosynthetic pathway; (2) promotion of YloS biosynthesis; or (3) complementation of a YloS mutant. In reference to the assays for identifying an antibiotic, a test compound "inhibits YloS protein activity" if it causes a decrease in YloS protein translation, yloS transcription or loss of YloS activity.

The test compounds of the present invention may be obtained using any of the numerous approaches in chemical compound library methods known in the art, including: natural compound libraries, biological libraries, spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam, K. S. (1997) *Anticancer Drug Des.* 12:145).

Examples of methods for the synthesis of molecular libraries may be found in the art, for example in: De Witt et al. (1993) *PNAS* 90:6909; Erb et al. (1994) *PNAS* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233. Libraries of compounds may be presented in solution, on beads, on chips, in bacteria, in spores (U.S. Pat. No. 5,223,409), on plasmids or on phage.

In one embodiment, the assay is a microorganism-based assay in which a recombinant microorganism that expresses a YloS protein or biologically active portion thereof is contacted with a test compound and the ability of the test compound to modulate YloS activity is determined. Determining the ability of a test compound to modulate YloS activity may be accomplished by monitoring, for example, growth, intracellular YloS concentrations or secreted YloS concentrations (as compounds that inhibit YloS will result in a buildup of YloS protein in the test microorganism). YloS substrate may be labeled with a radioisotope, enzymatic label or other soluble or insoluble signal generating moiety such that modulation of YloS activity may be determined by, e.g. detecting a conversion of labeled substrate to intermediate or product. For example, YloS substrates may be labeled with $^{32}$P, $^{14}$C or $^{3}$H, either directly or indirectly, and the radioisotope detected by direct counting of radioemission, by scintillation counting. Alternatively, the YloS substrates may be labeled directly or indirectly with a soluble or insoluble signal generating moiety and the signal detected by a calorimetric, enzymatic or fluorometric assay. Determining the ability of a compound to modulate YloS activity may alternatively be determined by detecting the induction of a reporter gene (comprising a y/oS-responsive regulatory element operatively linked to a nucleic acid encoding a detectable marker, e.g., luciferase) or detecting a CoA-regulated cellular response.

In another embodiment of the invention, the screening assay of the present invention is a cell-free assay in which the YloS protein or a biologically active portion thereof is contacted with a test compound in vitro and the ability of the test compound to bind to or modulate the activity of the YloS protein or biologically active portion thereof is determined. In one such embodiment, the assay includes contacting the YloS protein or biologically active portion thereof with known substrates to form an assay mixture, contacting the assay mixture with a test compound, and determining the ability of the test compound to modulate enzymatic activity of the YloS protein on its substrate. In one embodiment, the known substrate is the YloS protein. In another embodiment, the known substrate is a YloS analog. The phrase "YloS analog" means compounds similar in structure to the YloS protein that functions in the same or a similar manner as YloS. Exemplary analogs include labeled YloS protein and/or other detectable YloS protein derivatives. The term YloS analog also includes compounds closely related to or derived from the YloS protein, for example, structurally related compounds capable of acting as YloS substrate.

Screening assays may be accomplished in any vessel suitable for containing the microorganisms, proteins, and/or reactants. Examples of such vessels include microtiter plates, test tubes and micro-centrifuge tubes. In more than one embodiment of the assay methods of the present invention, it may be desirable to immobilize either the YloS protein, YloS substrate, substrate analogs or a recombinant microorganism expressing the YloS protein to facilitate separation of products, ligands, and/or substrates, as well as to accommodate automation of the assay. For example, glutathione-S-transferase/YloS fusion proteins may be adsorbed onto glutathione sepharose beads (Sigma Chemical Co., St. Louis, Mich.) or glutathione derivatized microtiter plates. Other techniques for immobilizing proteins on matrices (e.g., biotin-conjugation and streptavidin immobilization or antibody conjugation) may also be used in the screening assays of the invention.

This invention also includes novel agents identified by the above-described screening assays. Accordingly, it is within the scope of this invention to further use an agent identified as described herein in an appropriate animal model. For example, a YloS modulating agent identified as described herein (e.g., an anti-bactericidal compound) may be used in an infectious animal model to determine the efficacy, toxicity or side effects of treatment with such an agent and/or to treat a specific disease state caused or induced by a pathogenic microorganism. In a preferred embodiment, said novel agent is an antibiotic.

YloS modulators may further be designed based on the crystal structure of any one of the YloS proteins of the present invention. In particular, based, at least in part, on the discovery of YloS in many Gram$^+$ pathogenic bacteria, one may produce significant quantities of the YloS protein, for example using the recombinant methodologies as described herein, purify and crystallize the protein, subject the protein to X-ray crystallographic procedures and, based on the determined crystal structure, design modulators (e.g., active site modulators, for example, competitor molecules, active site inhibitors, and the like), and test the designed modulators according to any one of the assays described herein.

Some of the most important results of the present invention are summarized in the following figures.

Figure 3:
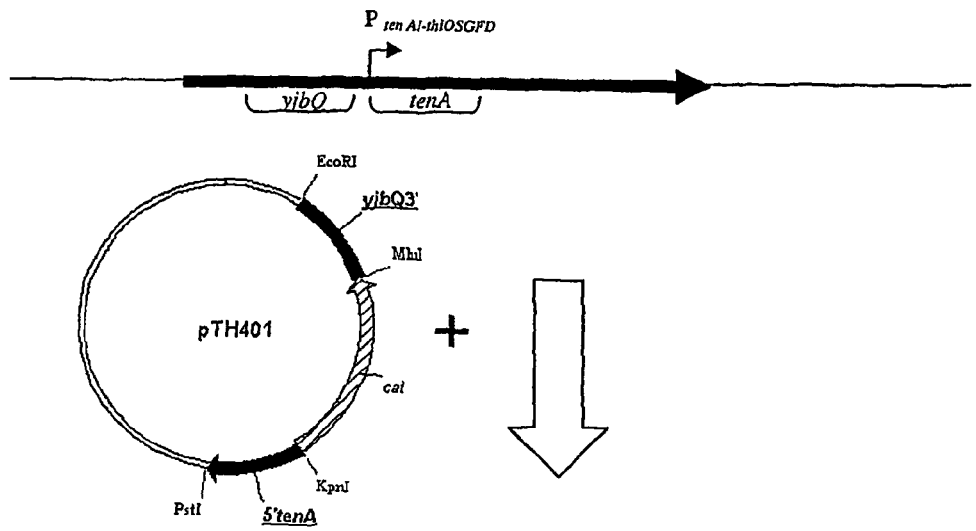
Figure 3:
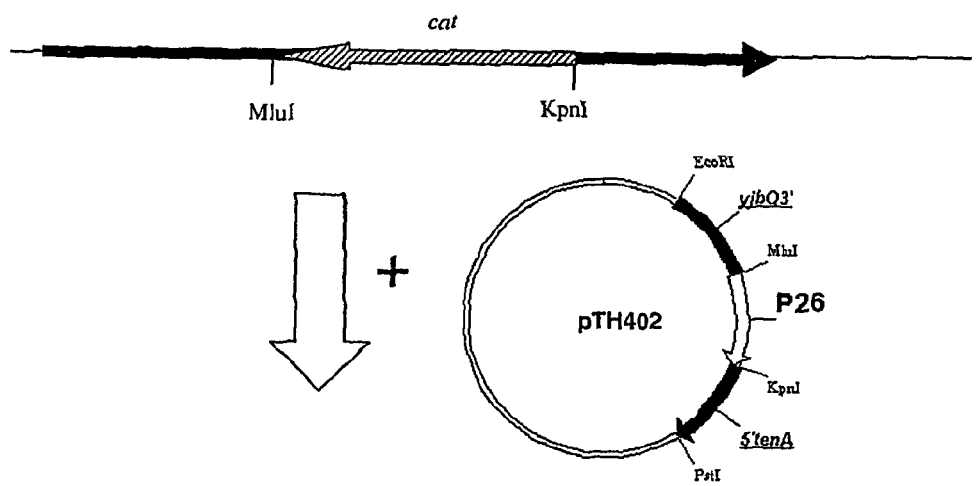
Figure 3:
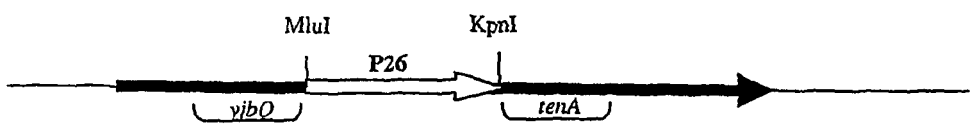

FIG. 3 describes the two-step procedure used to construct strain TH404, that overexpresses the *B. subtilis* thiB operon. In the first step, a thiamin-auxotroph strain was build by substitution of the thiB promoter region with a chloramphenicol acetyltransferase (cat) cassette. Restoration of prototrophy was then used to select for strains that have integrated the bacteriophage strong constitutive P26 promoter in front of the thiB operon.

The following examples are illustrative only and are not intended to limit the scope of the invention in any way.

EXAMPLE 1

General Methodology

Strains

*Bacillus subtilis* strains of the present invention are derived from strain PY79 (prototroph SPβ$^c$; Cat. #1A747, *Bacillus* Genetic Stock Center (BGSC), The Ohio State University, Columbus, Ohio 43210 USA) and 1012 (leuA8 metB5; Saito et al. (1979) *Mol. Gen. Genet.* 170:117-122). The neomycin-resistance gene (neo) cassette and tetracycline-resistance gene (tet) cassette were obtained from plasmid pBEST501 (Cat. #ECE47, BGSC) and pDG1514 (Cat #ECE100, BGSC), respectively.

Media

Standard minimal medium (MM) for *B. subtilis* contains 1× Spizizen salts, 0.04% sodium glutamate, and 0.5% glucose. Standard solid complete medium is Tryptone Blood Agar Broth (TBAB, Difco). Standard liquid complete medium is Veal Infusion-Yeast Extract broth (VY). For testing thiamin production in liquid test tube cultures, a thiamin-free medium is used (Difco). For fed-batch fermentations, VF medium is used. The compositions of these media are described below or are standard formula described previously (Harwood and Archibald (1990) pp. 1-26 and 545-552 (Appendix 1), In Cutting and Harwood (ed.) Molecular biological methods for *Bacillus*. John Wiley and Sons, New York).

TBAB medium: 33 g Difco Tryptone Blood Agar Broth, qsp 1 L water. Autoclave.

VY medium: 25 g Difco Veal Infusion Broth, 5 g Difco Yeast Extract, qsp 1 L water. Autoclave.

Minimum medium (MM): 100 ml 10× Spizizen salts; 10 ml 50% glucose; 1 ml 40% sodium glutamate, qsp 1 L water.

10× Spizizen salts: 140 g $K_2HPO_4$; 20 g $(NH_4)_2SO_4$; 60 g $KH_2PO_4$; 10 g $Na_3$(citrate).$2H_2O$; $MgSO_4.7H_2O$; qsp 1 L water.

Thiamin assay medium: 85 g Difco thiamin assay medium, qsp 1 L water. Autoclave (Difco Manual (1998) pp. 499-501, Difco Laboratories, Maryland, USA).

Trace elements solution: 1.4 g $MnSO_4.H_2O$; 0.4 g $CoCl_2.6H_2O$; 0.15 g $(NH_4)_6Mo_7O_{24}.4H_2O$; 0.1 g $AlCl_3.6H_2O$; 0.075 g $CuCl_2.2H_2O$; qsp 200 ml water. Filter-sterilize.

Fe-solution: 0.21 g $FeSO_4.7H_2O$; qsp 10 ml water. Filter-sterilize.

$CaCl_2$-solution: 15.6 g $CaCl_2.2H_2O$; qsp 500 ml water. Filter-sterilize.

Mg/Zn-solution: 100 g $MgSO_4.7H_2O$; 0.4 g $ZnSO_4.7H_2O$; qsp 200 ml water. Filter-sterilize.

VF fermentation medium: 0.75 g sodium glutamate; 4.71 g $KH_2PO_4$; 4.71 g $K_2HPO_4$; 8.23 g $Na_2HPO_4.12H_2O$; 0.23 g $NH_4Cl$; 1.41 g $(NH_4)_2SO_4$; 11.77 g Yeast extract (Merck); 0.2 ml Basildon antifoam; qsp 1 L water. Sterilize in place.

Added separately to the fermentor: glucose.$H_2O$ to 27.3 g/L final concentration.

Added separately to the fermentor (final concentrations): 2 ml/L trace elements solution; 2 ml/L $CaCl_2$-solution; 2 ml/L Mg/Zn-solution; 2 ml/L Fe-solution.

Modifications of the batch for feeding studies will be presented specifically in the following examples. Glucose was fed as needed. Feed solutions can contain minerals, defined or food nutrients, as reported in the following compositions:

Fermentation feeding solution for fed-batch process with NB (Nutrient Broth): Final concentrations (after autoclavation): 660 g/L glucose.$H_2O$; 2 g/L $MgSO_4$.$7H_2O$; 14.6 mg/L $MnSO_4$.$H_2O$; 4 mg/L $ZnSO_4$.$H_2O$; 47.8 g/L Nutrient Broth (Difco, autoclave separately in 1 g/ml solution).

Fermentation feeding solution for fed-batch process with HMP: Final concentrations (after autoclavation): 660 g/L glucose.$H_2O$; 2 g/L $MgSO_4$.$7H_2O$; 14.6 mg/L $MnSO_4$.$H_2O$; 4 mg/L $ZnSO_4$.$H_2O$. Add HMP to 0.54 g/L or 2.7 g/L (dissolve HMP in water/HCl conc.; filter-sterilize).

Fermentation feeding solution for fed-batch process with HET: Final concentrations (after autoclavation): 660 g/L glucose.$H_2O$; 2 g/L $MgSO_4$.$7H_2O$; 14.6 mg/L $MnSO_4$.$H_2O$; 4 mg/L $ZnSO_4$.$H_2O$. Add HET to 0.54 g/L or 2.7 g/L (dissolve HET in water; filter-sterilize).

Fermentation feeding solution for fed-batch process with HMP and HET: Final concentrations (after autoclavation): 660 g/L glucose.$H_2O$; 2 g/L $MgSO_4$.$7H_2O$; 14.6 mg/L $MnSO_4$.$H_2O$; 4 mg/L $ZnSO_4$.$H_2O$. Add HMP to 0.54 g/L or 2.7 g/L (dissolve HMP in water/HCl conc.; filter-sterilize). Add HET to 0.54 g/L or 2.7 g/L (dissolve HET in water; filter-sterilize).

Thiamin Assays

Biological assays: Total thiamin compounds were assayed using indicators derived from *Salmonella typhimurium* using known methods (Difco Manual (1998) pp. 499-501, Difco Laboratories, Maryland, USA). Strain DM456 (thiD906::MudJ) responds to thiamin, TMP and TPP in minimal medium, whereas strain DM1864 (thiL934::Tn10d) responds to only TPP (Webb and Downs (1997) *J. Biol. Chem.* 272: 15702-15707; Peterson and Downs (1997) *J. Bacteriol.* 179: 4894-4900). The response of DM456 to known amounts of thiamin, TMP, and TPP was similar, ranging from 0.0256 to 100 µg/liter. In addition, DM456 was found to be more sensitive to TPP than DM1854. To assay *B. subtilis* cultures, supernatants were filter-sterilized before preparation of dilutions. Intracellular thiamin levels were measured from dilutions of filter-sterilized cellular extracts that were obtained by French press-breaking of the cells and centrifugation at 10,000 g for 10 min. Indicator strains were grown overnight at 37° C. in thiamin assay medium (TAM). Turbidity readings were made at 600 nm and compared to a range of standard solutions.

HPLC/Thiochrome: Individual thiamin compounds, thiamin, TMP, and TPP were measured using a modified thiochrome-HPLC assay procedure described previously (Chie et al. (1999) Biochemistry 38:6460-6470). Briefly, 100 µl of culture supernatant or intracellular extracts are added to 200 µl of 4M potassium acetate. The sample is then oxidized by the addition of 100 µl fresh 3.8 mM potassium ferricyanide in 7 M NaOH. The mixture is vigorously mixed and then quenched by addition of 100 µl fresh 0.06% $H_2O_2$ in saturated $KH_2PO_4$. Samples are transferred to HPLC vials and injected onto a Supelcosil LC-18-T column (15 cm×4.6 mm, 3 µm) (Supelco—Ref. No 58970-U). Elution is made by a 10%-35% methanol ($H_2O$ 50%-25%) gradient in the presence of 40% 0.1 M $K_2HPO_4$ (pH 6.6) and 4 mM tetrabutyl ammonium hydrogen sulfate. Fluorescence is measured at 444 nm after excitation at 365 nm. The chronological order of elution from the column is thiamin, TMP, and TPP. This procedure was utilized to monitor both internal and external thiamin production during fermentation.

HPLC/DAD: To directly measure thiamin and the intermediates HMP and HET in the fermentation broth, chromatography of samples was performed on a Phenomenex LUNA C18 column, using an Agilent 1100 HPLC system equipped with a thermostatted autosampler and a diode array detector (DAD). The column dimensions are 150×4.6 mm, particle size 5 micron. The column temperature was kept constant at 20° C. The mobile phase is a mixture of 0.4 g pentane sulfonate in water, pH 2 (A) and methanol (B). Gradient elution is applied, ranging from 2% A (3 min) to 20% A in 20 minutes. The flow rate is 1 ml/min. The detection method is UV absorption at 254 nm. The selectivity of the method was verified by injecting 10 µl standard solutions of the relevant reference compounds, thiamin, HMP, and HET, each at 100 µg/ml. The target compounds were completely separated without special sample preparation.

Molecular and Genetic Techniques

Standard genetic and molecular biology techniques are generally know in the art and have been previously described (Maniatis et al. (1982) Molecular cloning: a laboratory manual. Cold Spring Harbor Laboratory, Cold Spring Harbor, N.Y.; Miller (1972) Experiments in molecular genetics. Cold Spring Harbor Laboratory, Cold Spring Harbor). DNA transformation, PBS1 generalized transduction, and other standard *B. subtilis* genetic techniques are also generally know in the art and have been described previously (Cutting and Horn (1990) pp. 27-74, In Cutting and Harwood (ed.) Molecular biological methods for *Bacillus*. John Wiley and Sons, New York).

Fermentations

Thiamin producing strains were grown in stirred tank fermentors, for example, in BIOFLO 4500 New Brunswick 20 liter vessels with 6-12 liter working volume. Computer control and data collection was done by NBS Biocommand 32 commercial software (New Brunswick Scientific Co., Inc., Edison, N.J., USA).

The inoculum size was usually 5% of the initial media volume in the vessel. A pH of 6.8 was kept constantly in the reactor by the automatic addition of ammonium hydroxide solution (28% in water). The fermentation temperature was 39° C. and a constant airflow of 6 liter/min was provided. Antifoam (Basildon) was added manually as needed and a constant pressure of 2 psi was kept in the vessel. A minimum concentration of 15%-dissolved oxygen ($pO_2$) was achieved by automatic cascading of the stirrer. The minimum stirrer speed was set to 400 rpm.

Fermentations can be batch processes but are preferably, carbohydrate-limited, fed-batch processes. Therefore a defined feed solution (s. above) was provided to the reactor after consumption of the initial glucose which was usually the case after 6-8 hours process time. At that time the pressure was increased to 8 psi and the addition of the feed solution was initiated at a rate of 70 g $h^{-1}$ increasing linearly to 102.5 g $h^{-1}$ in a period of 8 hours and then kept constant at 102.5 g $h^{-1}$.

EXAMPLE 2

Culturing Mutant Microorganisms Producing Thiamin and Thiamin Compounds De Novo

This example describes the isolation of thiamin biosynthesis and deregulation mutations ΔthiL, tx1, tx26 mutations and their combination to produce a *B. subtilis* strain that overproduces thiamin compounds.

Intra- and extracellular levels of thiamin products from wild type and engineered *B. subtilis* strains were determined from cells grown in 30 ml minimal medium shake flasks cultures at 37° C. for 24 hours. As a positive control, thiamin deregulated E. coli PT-R1 mutant was also tested. Bioassay results indicated that thiamin products were readily detected from extracts of sonicated cells, but little or none were detected from the culture medium (Table 1). The intracellular level of thiamin products in logarithmic or stationary phase wild-type B. subtilis was calculated to be approximately 100-200 µg/L. As reported for E. coli, intracellular thiamin products in B. subtilis are likely to be in the form of TPP. Intracellular levels of thiamin products were significantly higher in the thiamin deregulated E. coli PT-R1 strain, reaching approximately 1.6 mg/L in stationary phase cells.

TABLE 1

Thiamin production in various E. coli and B. subtilis strains.

| Strain | Extracellular[a] (µg/L) | Intracellular[b] (µg/L) | Predicted Extracellular[c] |
|---|---|---|---|
| E. coli K-12 | <0.1 | 80 | 3 |
| E. coli PT-R1 | 6 | 1600-2800 | 50-90 |
| B. subtilis prototroph | <0.1 | 100-200 | 3-6 |

[a]Thiamin concentration in minimal medium (30 ml) after 24 hours growth at 37° C.
[b]Thiamin concentration of 1 ml supernatant of sonicated cells collected from a 30 ml minimal medium culture after 24 hours growth at 37° C.
[c]Assumes all intracellular thiamin products are excreted into the culture medium. Calculation: (Intracellular thiamin concentration (µg/L) × 0.001 L) × 1000 ml/L/30 ml.

Comparison of the E. coli ThiL protein sequence to the protein database of Subtilist detected significant similarity to only one protein sequence: YdiA (P(N)=8.1e$^{-5}$). The gene encoding this protein, ydiA, is 975 base pairs in length and is the first gene of a five-gene operon located at 55° on the B. subtilis chromosome. Non-polar insertional vectors pMU-TIN2 and 4, which contain an IPTG-inducible $P_{spac}$ promoter that controls transcription of genes downstream from the site of insertion, were used to generate thiL disruption mutants (Vagner et al. (1998) Microbiology 144:3097-3104). Using two oligonucleotide primers, BsuydiA1 (SEQ ID NO: 7) and BsuydiA2 (SEQ ID NO: 8), corresponding to the YdiA sequence between nucleotides 264 and 612, a 348 bp DNA fragment was prepared by standard PCR methods. This fragment was cloned between the HindIII and BamHI sites of pMUTIN2 vector, generating the E. coli plasmid pTH1. This plasmid was then inserted into the ydiA (thiL) gene of B. subtilis PY79 by DNA transformation selecting for colonies resistant to 5 µg/ml erythromycin. One Erm$^r$ colony was recovered and named TH5 (ΩthiL::pMUTIN). By comparing bacterial growth on TBAB medium with erythromycin in the presence or absence of IPTG, it was determined that expression of one or more of the genes downstream of ydiA was required for cell growth. Similar results were also obtained when additional ydiA (thiL) disruptions were generated by inserting a chloramphenicol acetyltransferase cassette containing ($cat_2$) or lacking ($cat_4$) the endogenous rho-independent transcription termination site between nucleotide 267 and 272 of ydiA (thiL). PCR primer pairs cat#1 (SEQ ID NO: 9)-cat#2 (SEQ ID NO: 10) and cat#1-cat#4 (SEQ ID NO: 11) were used to generate DNA cassettes $cat_2$ or $cat_4$ gene, respectively, which were ligated to ydiA (thiL) PCR DNA fragments generated using primers ydiA/atp/for/bam (SEQ ID NO: 12)—ydiA/atp/rev/sma (SEQ ID NO: 13) and ydiA/ctp/for/sma/2 (SEQ ID NO: 14)—ydiA/ctp/rev/ecorI/2 (SEQ ID NO: 15). The ΔthiL::cat cassettes were then inserted directly into the chromosomal ydiA (thiL) gene of strain PY79 by DNA transformation selecting for colonies resistant to 5 µg/ml chloramphenicol. Only Cm$^r$ colonies containing ΔthiL::$cat_4$ (TH12) grew normally on TBAB medium; Cm$^r$ colonies containing ΔthiL::$cat_2$ grew as tiny, pinpoint colonies. Strains TH11 and TH12 containing ΔthiL::$cat_2$ and AydiA::$cat_4$ were saved, respectively. Surprisingly, strains TH5 and TH12 were not thiamin or TPP auxotrophs. Instead both strains were thiamin bradytroph: on minimal medium the colony size of TH5, and TH12 was half the diameter of PY79 control colonies. Since thiL null mutants of Salmonella and E. coli are strict thiamin auxotrophs, B. subtilis appeared to contain a second kinase activity or an alternate route that could convert TMP to TPP. Interestingly, ydiA (thiL) mutants were able to cross-feed B. subtilis thiF or thiG mutants (strains called respectively TH3 and TH4) on minimal medium after one day of incubation at 37° C., whereas PY79 took three or more days. This suggested that ydiA mutants are partially deregulated for thiamin biosynthesis and release more diffusible thiamin products than the wild-type strain. Bioassay results (Table 2) showed that the total intracellular thiamin production (thiamin+TMP+TPP) level was slightly higher (2- to 3-fold) in TH5 and TH12 than PY79. Slightly higher total thiamin levels were also detected in the culture medium relative to PY79, but well below the intracellular levels. Interestingly, the increase in thiamin production was not sufficient to provide resistance to the thiamin analog pyrithiamine.

TABLE 2

Thiamin production of B. subtilis thiL insertional mutants.

| Strain | thiL mutation | Extracellular[a] (µg/L) | Intracellular[b] (µg/L) |
|---|---|---|---|
| B. subtilis PY79 | — | <0.1 | 190 |
| B. subtilis TH5 | ΩthiL::pMUTIN2 | 0.7 | 550 |
| B. subtilis TH12 | ΔthiL::$cat_4$ | 0.9 | 530 |

[a]Thiamin concentration in minimal medium (30 ml) after 24 hours growth at 37° C.
[b]Thiamin concentration of 1 ml supernatant of sonicated cells collected from a 30 ml minimal medium culture after 24 hours growth at 37° C.

The strategy to isolate thiamin deregulated mutants of B. subtilis was to mutagenize bacteria that contained a thiA-lacZ fusion and then screen for colonies on XGAL-containing medium that were Lac$^+$ (i.e. blue colonies) in the presence of TPP or thiamin. A 732 bp-long DNA fragment containing 417 bp of the 5' promoter region of thiA was prepared by PCR using standard methods and cloned unidirectionally in front of the promoterless lacZ gene of the pDG1728 vector (Guerout-Fleury et al. (1996) Gene 180:57-61), resulting in plasmid pTH12. This vector is designed to introduce ectopic transcriptional lacZ fusions into the non-essential amyE locus of B. subtilis. Plasmid pTH12 was linearized by restriction enzyme digestion and transformed into B. subtilis PY79, selecting for colonies that were resistant to 100 µg/ml spectinomycin. One resulting colony, designated TH21 (ΩamyE:: thiA-lacZ), showed unambiguous thiamin regulation when tested under different nutrient growth conditions. When grown to early logarithmic phase (OD600=0.8-0.9) in shake-flask cultures containing 1 µM thiamin, the expression of thiA-lacZ was repressed approximately 80-fold compared to cells grown in minimal medium without thiamin. HMP (1 µM) also repressed expression of the fusion, but to a lesser extend (6- to 7-fold). Both thiazole and adenosine (1 µM each) showed repressing activity. In a time course experiment, expression of thiA-lacZ was highest (200 Miller Units) when cells were at early logarithmic phase (OD600=0.8-0.9). Expression gradually decreased (to 50 Miller Units) when cells enter stationary phase (OD600≧1).

The regulation of thiA-lacZ fusion was also assessed in several mutants. In a sporulation-deficient mutant strain (ΔspoOA::erm), expression of the fusion was regulated, however, the level of repression by thiamin was less than in the wild type. In strains containing a deletion of ydiA/thiL (TH22 (ΔthiL::cat$_4$, ΩamyE::thiA-lacZ)), the fusion was partially deregulated: LacZ activity was 2- to 3-fold higher under both repressing and derepressing growth conditions.

Based on these results, thiA-lacZ reporter strain TH22 (ΔthiL::cat$_4$) was used to screen for deregulated mutants under repressing growth conditions. Two methods were used to isolate such mutants. In the first method, MM agar plates were prepared that contain 1 μM thiamin and 25 μg/ml XGAL. After applying a uniform dilution of logarithmic growth phase TH22 cells, a paper disk containing 3 drops of ethylmethane sulfonate (EMS, d=1.17 g/ml solution) was placed in the center of the plate. Lac$^+$ colonies appeared over a period of 7 days incubation at 37° C. Deregulated mutants Tx1-Tx10 were recovered. In the second method banks of EMS-mutagenized cells were prepared and screened. Accordingly, logarithmic stage TH22-cells were treated with 9.4 mM EMS for 90 minutes and aliquots frozen in 10% glycerol at −90° C. Cells from the frozen stocks were diluted in VY medium, incubated at room temperature for 30 minutes and then plated onto MM medium containing 1 μM thiamin and 25 μg/ml XGAL. Screening of Lac$^+$ colonies led to mutants Tx11 to Tx26. These mutants could be grouped into three classes based on the intensity and timing of the appearance of blue color under thiamin- and TPP-repressing conditions (Table 3), and based on additional phenotypes. One mutant (Tx1) was found to be a strong thiamin bradytroph suggesting that this mutation either inactivated (1) a residual TMP kinase activity, or (2) a gene involved in a second TMP to TPP route, via TMP. Another mutant, Tx26, was resistant to 10 μM pyrithiamine. In terms of synthesis of thiamin products, mutant Tx7 (class 2) excreted 2- to 3-times more total thiamin products relative to the parental strain, TH22 (ΔthiL::cat$_4$, ΩamyE::thiA-lacZ), although the intracellular levels of thiamin products were similar (Table 4). Mutant Tx26 (class 1), excreted 10- to 15-times more total extracellular thiamin products into the culture medium than the TH22 control strain (Table 4). Little over 50% of the excreted thiamin products were in the form of TPP. Class 3 mutants, represented by Tx1 and Tx23, appear to be affected in the thiamin-TMP-TPP pathway based on the differential Lac expression in the presence of thiamin or TPP.

TABLE 3

Phenotype of *B. subtilis* thiamin-deregulated mutants.

| Class | Phenotype | Mutant |
|---|---|---|
| 1 | Thiamin prototroph with strong Lac activity after 1 day growth on minimal medium containing either thiamin or TPP | Tx2; Tx4; Tx6; Tx9; Tx11; Tx12; Tx13; Tx14; Tx15; Tx16; Tx17; Tx21; Tx22; Tx24; Tx26 |
| 2 | Thiamin prototroph with weak Lac activity after >3 days growth on minimal medium containing thiamin, and weak or no Lac activity in the presence of TPP | Tx3; Tx5; Tx7; Tx8; Tx10; Tx25 |

TABLE 3-continued

Phenotype of *B. subtilis* thiamin-deregulated mutants.

| Class | Phenotype | Mutant |
|---|---|---|
| 3 | Thiamin auxotroph (or strong bradytroph) with strong Lac activity after 1 day growth on minimal medium containing thiamin or TMP, but little or no Lac activity in the presence of TPP | Tx1 and Tx23 |

TABLE 4

Thiamin production of *B. subtilis* thiamin-deregulated mutants.

| Strain | Extracellular[a] (μg/L) | Intracellular[b] (μg/L) |
|---|---|---|
| *B. subtilis* PY79 | <0.1 | 150 |
| *B. subtilis* TH22 | 1 | 500 |
| *B. subtilis* Tx7 | 5 | 500 |
| *B. subtilis* Tx26 | 15 | 500 |

[a] Thiamin concentration in minimal medium (30 ml) after 24 hours growth at 37° C.
[b] Thiamin concentration of 1 ml supernatant of sonicated cells collected from a 30 ml minimal medium culture after 24 hours growth at 37° C.

In exogenous precursor feeding studies, conversion of HMP and HET to total thiamin products also differed between Tx7 and Tx26 (Table 5). Each strain was grown in minimal medium cultures containing the indicated amounts of HET and HMP for 18 hours at 37° C. Culture media and cell extracts were analyzed for thiamin production. (Thiamin+TMP+TPP) and (TPP) were measured by a biological assay using *S. typhimurium* indicators DM456 (ΩthiD906::MudJ) and DM1856 (ΩthiL934::Tn10), respectively. Thiamin products were not detected in the medium. In Tx7, most of the thiamin products were found within the cells, predominantly in the form of TPP. In contrast, 90% of the total thiamin products in Tx26 was found in the culture medium mostly as thiamin+TMP. Extracellular accumulation was approximately 40-fold higher than Tx26 grown without added HMP+HET.

TABLE 5

HMP and HET feeding studies of *B. subtilis* thiamin-deregulated mutants Tx7 and Tx26.

| | | | | Extracellular (μg/L) | | Intracellular (μg/L) | |
|---|---|---|---|---|---|---|---|
| Strain | HMP (10 μM) | HET (10 μM) | OD$_{600}$ | Thiamin + TMP + TPP | TPP | Thiamin + TMP + TPP | TPP |
| Tx7 | − | − | 1.3 | 0.2 | 0 | 750 | 360 |
| Tx7 | + | − | 1.1 | 0.3 | 0 | 210 | 390 |
| Tx7 | − | + | 1.5 | 0.3 | 0 | 890 | 1400 |
| Tx7 | + | + | 1.2 | 4 | 8 | 1800 | 2000 |
| Tx26 | − | − | 1.2 | 2 | 0.8 | 500 | 280 |
| Tx26 | + | − | 1.7 | 40 | 18 | 610 | 640 |
| Tx26 | − | + | 1.1 | 2 | 0.6 | 420 | 240 |
| Tx26 | + | + | 1.2 | 80 | 10 | 610 | 650 |

A *B. subtilis* strain was built that contains a combination of mutations tx26, thiL, and tx1. This strain could serve as a host for integrated and amplified engineered thiamin biosynthetic genes. As a first step, the mutations in Tx26 were transferred into TH12 (ΔthiL::cat$_4$) by DNA transformation and selecting colonies that were resistant to 10 μM pyrithiamine. One Pyr$^r$ colony that was also Lac$^+$ in the presence of thiamin was recovered and designated TH48. Each strain was grown in minimal medium supplemented with micronutrients and 2.5% Difco nutrient broth (NB) for 18 hours at 37° C. Supernatants were analyzed for thiamin production by bioassays using indicators *Salmonella* DM456 (thiD906::MudJ) for (Thiamin+TMP+TPP) and *Salmonella* DM1856 (thiL934::Tn10) for (TPP). When grown in minimal medium shake-flask cultures, TH48 produced similar levels of thiamin products compared to the Tx26 parent (Table 6). The cat-interrupted thiL gene was next replaced by an in-frame deletion. Using standard PCR methods, an in-frame deletion of thiL (removing amino acid residues Gly79 and Gly202) was first constructed and inserted between the BamHI and EcoRI sites of the *E. coli* plasmid vector pEpUCΔ1 creating pTH30. pEpUCΔ1 (S. Seror, Université Paris-Sud, 91405 Orsay, France) contains a selectable erythromycin-resistance (erm) cassette and a temperature-sensitive origin of replication that does not function over 51° C. TH48 cells were transformed at 51° C. with pTH30 selecting for erythromycin resistance. One Erm$^r$ colony that was also Cm$^r$ was recovered and was grown overnight at 28° C. in the absence of antibiotic selection for 72 hours. Bacteria were then plated onto TBAB agar plates, and the plates incubated overnight at 37° C. Approximately 25% of the colonies were found to be sensitive to both erythromycin and chloramphenicol antibiotics. PCR analysis of chromosomal DNA from several Erm$^S$ Cm$^S$ colonies confirmed the presence of the in-frame ΔthiL mutation and the absence of the ΔthiL::cat$_4$ mutation. This resulted in strain TH83. The tx1 mutation was next introduced by transduction into TH83 by PBS1 transduction by standard procedures using linkage to a silent Tn917 insertion, ΩyloA::Tn917 (60% linkage to tx1; strain 1A633 of the *Bacillus* Genetic Stock Center, also called CU4153 or Qzdi-82::Tn917). The resulting strain was called TH95.

TABLE 6

Thiamin production of *B. subtilis* thiamin-deregulated strains containing ΔthiL and tx26 mutations.

| Strain | Genotype | OD$_{600}$ | Extracellular (μg/L) Thiamin + TMP + TPP | TPP |
|---|---|---|---|---|
| Tx26 | ΔthiL::cat$_4$ thiA-lacZ tx26 | 16.5 | 320 | 460 |
| TH48 | ΔthiL::cat$_4$ tx26 | 18.7 | 280 | 310 |
| TH49 | ΔthiL::cat$_4$ thiA-lacZ tx26 | 16.5 | 300 | 470 |
| TH12 | ΔthiL::cat$_4$ | 18.4 | 2.6 | 2.2 |
| TH22 | ΔthiL::cat$_4$ thiA-lacZ | 18.4 | 3.2 | 2.4 |

In standard fed-batch fermentations using 20-liter lab scale fermentors, NB was found to enhance thiamin production in TH95. Results showed that extracellular thiamin product levels were approximately 2- to 3-fold higher using feed medium containing 4% NB compared to feed without NB (Table 7). Production reached a maximum level of 6-7 mg/liter between 30-48 hours of growth. More importantly, as judged by thiochrome/HPLC assay, at least 65% of extracellular thiamin products were in the form of thiamin, whilst in the fermentation without NB in the feed, most of the product was TMP and TPP. Simultaneously, increasing the amount of NB in the seed (10%) and removing NB from the feed, delayed production of thiamin-related products to 24 hours cultivation time. Moreover, excreted thiamin products were decreased and mainly in the form of TMP. Addition of NB (4%) to the batch also led to a decrease in total thiamin production and a change in the excretion profile, in which all the thiamin forms (THI, TMP, and TPP) were in almost equimolar quantities.

TABLE 7

Thiamin production of TH95 in 6-liter fermentation with the addition of nutrient broth (NB).

| | | | Thiamin products (mg/L) | | |
|---|---|---|---|---|---|
| Strain | Feed 60% Glucose plus | OD$_{600}$ 48 hr | Thiamin 48 hr | TMP 48 hr | TPP 48 hr |
| TH95 | — | 120 | 0.7 | 1.4 | 1.0 |
| TH95 | 4% NB | 140 | 4.5 | 1.0 | 1.2 |

EXAMPLE 3

Producing Thiamin Compounds Using HMP and HET

This example describes a method to produce thiamin compounds growing thiamin-deregulated strains in the presence of thiamin precursors HMP and HET.

Fermentation of strain TH95 (tx26 tx1 ΔthiL yloA::Tn917) with thiamin precursor co-feed was performed in 6- and 1-liter scale under fed-batch conditions. Feed solutions containing 0.54 g/liter hydroxyethylthiazole (HET) and 0.54 g/liter hydroxymethylpyrimidine (HMP) led to a significant accumulation of thiamin in the culture medium. Thiamin titers reached 120 mg/L (Table 8) after 48 hours, which represents a molar yield of 25% based on the concentration of either precursor. Conversely, TMP and TPP titers were very low (4 and 2 mg/liter, respectively) accounting for less than 3% of the total amount of thiamin-related excreted products. Feeding of either HMP or HET alone led to a very low titer of all thiamin products. Increasing the concentration of HMP and HET to 2.7 g/liter each or in combination did not result in a significant increase in thiamin production levels. Extending the fermentation of TH95 in the presence of 0.54 g/liter HET and 0.54 g/liter HMP led to a preferential increase in thiamin titers. After 70 hours, thiamin (THI) titers reached 250 mg/liter whereas TMP and TPP levels (7 and 2 mg/liter) were similar to those at the 48-hour time point (Table 9).

TABLE 8

Thiamin production of TH95 in 6-liter fermentation with the addition of HMP or HET.

| | | | Thiamin products (mg/L) | | |
|---|---|---|---|---|---|
| Strain | Feed: 60% Glucose plus | OD$_{600}$ 48 hr | Thiamin 48 hr | TMP 48 hr | TPP 48 hr |
| TH95 | 0.54 g/L HMP | 80 | 6 | 1 | 0.8 |
| TH95 | 0.54 g/L HMP, 0.54 g/L HET | 90 | 120 | 4 | 2 |
| TH95 | 0.54 g/L HET | 70 | 1 | 0.5 | 0.3 |
| TH95 | 2.7 g/L HMP | 110 | 7 | 1 | 1 |
| TH95 | 2.7 g/L HMP, 2.7 g/L HET | 80 | 125 | 12 | 4 |
| TH95 | 2.7 g/L HET | 90 | 3 | 1 | 1 |

TABLE 9

Thiamin production of TH95 in 1-liter fermentation with the addition of HMP and HET.

| | | | | Thiamin products (mg/L) | | | | |
|---|---|---|---|---|---|---|---|---|
| Strain | Feed 60% Glucose plus | OD$_{600}$ 48 hr | OD$_{600}$ 70 hr | THI 48 hr | TMP 48 hr | TPP 48 hr | THI 70 hr | TMP 70 hr | TPP 70 hr |
| TH95 | 0.54 g/L HMP, 0.54 g/L HET | 75 | 85 | 110 | 4 | 2 | 250 | 7 | 2 |

| Strain | Feed 60% Glucose plus | OD$_{600}$ 48 hr | OD$_{600}$ 70 hr | THI 48 hr | TMP 48 hr | TPP 48 hr | THI 70 hr | TMP 70 hr | TPP 70 hr |
|---|---|---|---|---|---|---|---|---|---|
| TH95 | 0.54 g/L HMP, 0.54 g/L HET | 75 | 85 | 110 | 4 | 2 | 250 | 7 | 2 |

EXAMPLE 4

Thiamin Producing Strains With Increased ThiA Synthesis

This example describes the construction of a DNA cassette containing the *B. subtilis* thiA gene which can be used to overexpress said gene resulting in overproduction and excretion of thiamin products.

Figure 1:
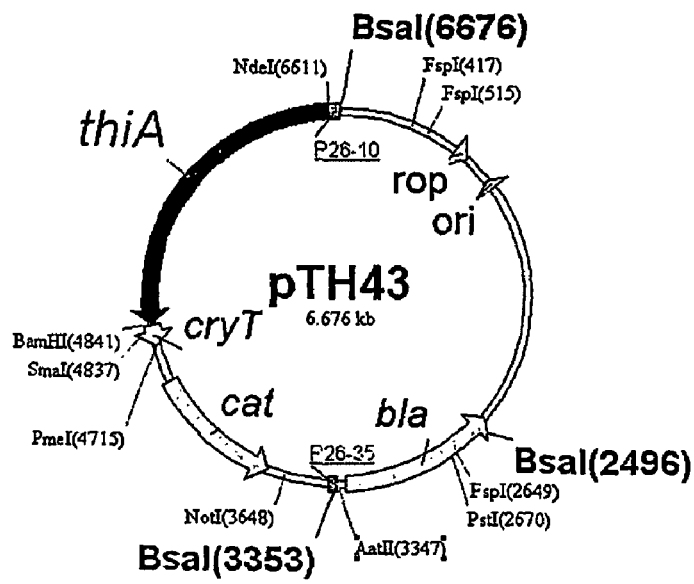
FIG. 1 depicts the structure of the $P_{26}$ thiA expression cassette contained in plasmid pTH43 with a chloramphenicol-resistance gene (A) and plasmid pTH47 with a tetracycline resistance gene (B).
Figure 1:
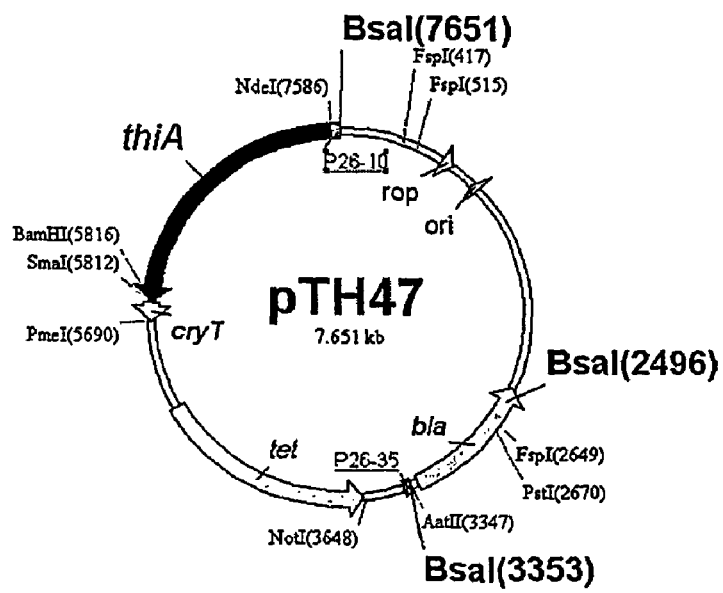

In order to increase expression, an amplifiable engineered thiA cassette was constructed in which the native promoter region was replaced by a strong constitutive SP01-26 promoter derived from the *B. subtilis* bacteriophage SPO1 (designated $P_{26}$). First a 1770 bp-long DNA fragment containing the entire thiA gene was amplified by PCR using standard methods and synthetic oligo DNA primers thiA/for/pXI22/NdeI (SEQ ID NO:1) and thiA/rev/pXI22/Bam (SEQ ID NO: 2). After digestion with NdeI and BamHI, the PCR product was inserted between the NdeI and BamHI sites of pXI22mod and transformed into competent *E. coli* cells using standard methods. pXI22mod is a 7.2 kb *E. coli* plasmid that contains the $P_{26}$ promoter, a synthetic *Bacillus* RBS, cryT terminator, selectable ampicillin (bla) resistance and chloramphenicol (cat) resistance genes, and NdeI/BamHI cloning sites located between the RBS and cryT terminator (the NdeI site generates the ATG start site). The $P_{26}$ promoter is inactivated due to the placement of the *E. coli* ColE1 replicon and the bla gene between the –35 and –10 consensus regions of the promoter. In addition, a NdeI site within pXI22 was modified by standard methods to remove an undesired NdeI restriction site located within the replicon region. This resulted in plasmid pTH43 (FIG. 1). Another thiA expression cassette was also prepared by replacing the cat cassette with a selectable tetracycline-resistance (tet) gene. To do this, a 2042 bp DNA fragment containing the tet gene from plasmid pDG1514 (BGSC, Cat #ECE100) gene was amplified by PCR using standard methods and synthetic oligo DNA primers tet/for/PmeI (SEQ ID NO: 3) and tet/rev/NotI (SEQ ID NO: 4). This fragment was then cloned between the PmeI and NotI sites of pTH43 to give pTH47 (FIG. 1).

The next task was to integrate the $P_{26}$ thiA-cat cassette in thiamin deregulated strains. First, plasmid pTH43 was digested by BsaI and a 3352 bp long fragment was purified from the agarose gel using standard methods. The purified fragment was ligated to itself at high DNA concentration and transformed into TH95 competent cells using standard methods. Transformants were selected on TBAB medium containing 5 µg/ml chloramphenicol. One Cm$^r$ colony, designated TH116, was saved for further studies. The expression of thiA was increased by obtaining colonies that were resistant to successively higher levels of chloramphenicol. Specifically, a strain of TH116 resistant to 60 µg/ml chloramphenicol could be obtained. SDS-PAGE analysis of crude cell extracts of TH116 strains resistant to 60 µg/ml chloramphenicol showed significantly higher levels of ThiA protein than TH116 strains resistant to only 5 µg/ml chloramphenicol.

Thiamin production with the TH116 engineered strain was tested in 20-liter lab scale fermentors using standard fed-batch conditions with HET co-feeding (0.54 g/liter, w/w). Strain TH116 resistant to 60 µg/ml chloramphenicol produced between 18-21 mg/liter thiamin (Table 10), which is a 3-fold increase in thiamin production compared to TH95 fermentation (Table 8). Thiamin production, however, was significantly lower than observed in feeding studies (see Example 3). This result indicates that formation of HMP is rate limiting, which could be caused by insufficient quantities of an additional enzymatic activity or low levels of AIR pools.

TABLE 10

Thiamin production of TH116 in 6-liter fermentation.

| | | Thiamin products (mg/L) | | | | |
|---|---|---|---|---|---|---|
| Strain | OD$_{600}$ 48 hr | Thiamin 24 hr | TMP 24 hr | TPP 24 hr | Thiamin 48 hr | TMP 48 hr | TPP 48 hr |
| TH116 | 65 | 18 | 4 | 6 | 21 | 3 | 5 |

EXAMPLE 5

Methods for Producing Thiamin Compounds Using Microorganisms with Increased AIR Formation This example describes experiments that increase thiamin production by altering the purine pathway to increase aminoimidazole ribotide (AIR) formation. This was achieved by simultaneously deregulating the expression of the *B. subtilis* purine operon using a mutation within the leader region of the purine operon (purO) and blocking conversion of AIR to carboxyaminoimidazole ribotide (CAIR) through introduction of a mutation within the purE gene encoding phosphoribosylaminoimidazole carboxylase I.

To construct a purO mutation, the upstream region of the operon promoter was amplified by PCR using primers YebF+1 (SEQ ID NO: 18) and YebG-1 (SEQ ID NO: 19) to generate a 667-bp product. Genomic DNA prepared from wild-type *B. subtilis* 1012 was used as a template and the PCR reaction conditions consisted of 30 cycles of denaturation at 95° C. for 1 min., annealing at 55° C. for 1 min. and extension at 72° C. for 1 min. The PCR product was purified using the Wizard PCR purification kit (Promega) and double-digested with EcoRI-BamHI. The PCR product was cloned into EcoRI-BamHI-digested pUC19 to give plasmid pNMR72.

The purE promoter was amplified by PCR using primers PurE+3 (SEQ ID NO: 20) and PurE-1 (SEQ ID NO: 21) to give a 768-bp product. The PCR product was purified using the Wizard PCR purification kit (Promega) and double-digested with BamHI-PstI and cloned into BamHI-PstI-digested pNMR72 generating plasmid pNMR76.

Plasmid pNMR76 was linearized with BamHI and ligated to a BclI-digested neomycin-resistance (neo) gene cassette from pBEST50 to give plasmids pNMR79, with the neo cassette in the same orientation as pur transcription, and pNMR80, with the neo cassette in the opposite orientation. Both plasmids were linearized with ScaI and transformed into competent *B. subtilis* 1012 cells. Transformants were selected on TBAB plates containing neomycin to a final concentration of 2.5 μg ml$^{-1}$. 67 colonies were observed for the pNMR79 transformation, and 18 colonies for the pNMR80 transformation. 6 colonies from each transformation experiment were picked and analyzed by PCR. Two clones were identified as containing the truncated pur operons integrated as double crossovers for each transformation. These clones were renamed BS1566 and BS1567 for the pNMR79 transformation, and BS1568 and BS1569 for the pNMR80 transformation.

To combine the purO deletion mutation with the purE6 mutation, *B. subtilis* strain 1A320 (purE6 trpC2; Bacillus Genetic Stock Center, The Ohio State University, Columbus, Ohio 43210 USA) was transformed with chromosomal DNA from strain BS1567, resulting in strain TH94. Since purO::neo purE6 are closely linked, both mutations were simultaneously transferred to thiamin deregulated strain TH95 by PBS1 generalized transduction under standard conditions, resulting in strain TH101 (tx26 tx1 ΔthiL yloA::Tn917 ApurO::neo purE). To determine thiamin production, strain TH101 was grown under standard 1-L fed-batch conditions with a HET (0.54 g/liter) co-feeding. Xanthine was also added to the batch medium and feed solution at 0.01% (w/w) and 1% (w/w, dissolved in 7.35 N NaOH), respectively, to satisfy the purine requirement. Xanthine does not feedback inhibit any of the purine de novo enzymes, nor is it toxic at high concentrations. In addition, the feed also contained NH$_4$Cl (9.6% w/w) and the pH was controlled using H$_2$SO$_4$ (10%) and NaOH (7.35 M). Results indicated that TH101 produced approximately 6-times more thiamin in the broth than the control TH95 fermentation under the same experimental conditions (Table 11).

TABLE 11

Thiamin production of TH95 in 1-liter fermentation containing the purOE mutations.

| Strain | purOE-deletion | OD$_{600}$ 48 hr | Thiamin products mg/L | | |
|---|---|---|---|---|---|
| | | | Thiamin | TMP | TPP |
| TH95 | − | 90 | 0.5 | 0.5 | BD |
| TH101 | + | 52 | 2.7 | 0.6 | 0.3 |

BD, below detection

EXAMPLE 6

Methods for Increasing Thiamin Compounds Production by Enhancing the Thiamin Coupling Gene This example describes the construction of a DNA cassette containing the *B. subtilis* thiC gene which can be used to overexpress said gene resulting in overproduction and excretion of thiamin products. This gene is located in an operon containing thiK, a gene that encodes the salvage enzyme, HET kinase.

Figure 2:
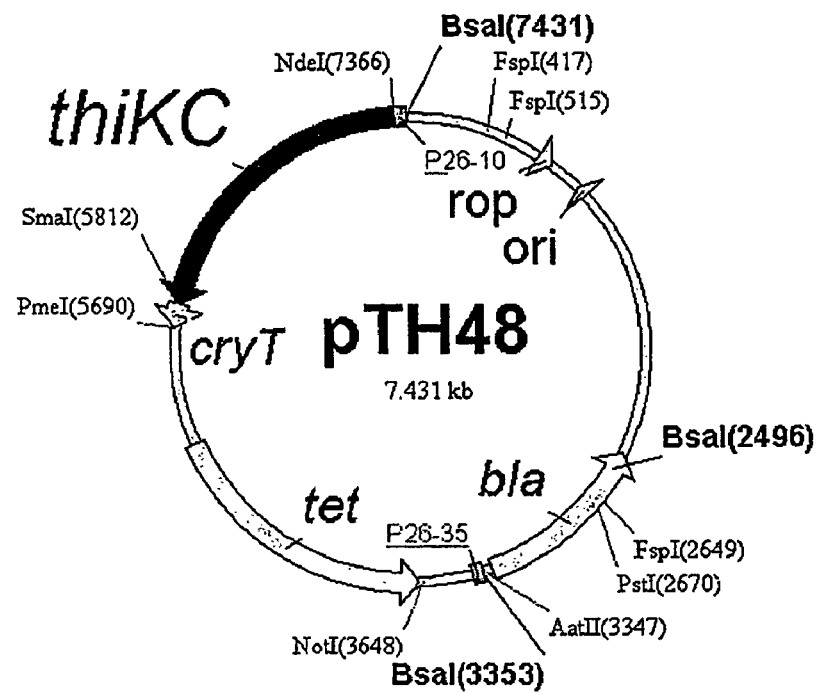
FIG. 2 depicts the structure of the $P_{26}$ thiKC expression cassette contained in plasmid pTH48 with a tetracycline resistance gene.

In order to increase expression of thiC, an amplifiable cassette was constructed in which the native promoter region was replaced by a strong constitutive SP01-26 promoter derived from the *B. subtilis* bacteriophage SPOL (designated P$_{26}$). To do this, the thiA cassette was removed from pTH47 and replaced by a DNA fragment containing thiKC. First a 1555 bp fragment containing thiKC structural gene was amplified by PCR using standard methods and synthetic oligo DNA primers thiKC/for 3/pXI22/NdeI (SEQ ID NO: 5) and thiCop/rev2/pXI22/SmaI (SEQ ID NO: 6). After digestion with NdeI and BamHI, the PCR product was inserted between the NdeI and BamHI sites of pTH43, resulting in plasmid pTH48 (FIG. 2).

This P$_{26}$ thiKC-tet cassette was introduced into TH95 by first digesting pTH48 with BsaI and purifying a 4078 bp fragment from the agarose gel using standard methods. The purified fragment was ligated to itself at high DNA concentration and transformed into TH95 competent cells using standard methods. Transformants were selected on TBAB medium containing 20 μg/ml tetracycline. One Tetr colony, designated TH115, was saved for further study. The expression of thiKC was increased by obtaining colonies that were resistant to successively higher levels of tetracycline. Specifically, a strain of TH115 resistant to 45 μg/ml tetracycline could be obtained. SDS-PAGE analysis of crude cell extracts showed significantly higher levels of ThiK and ThiC protein than TH115 strains resistant to only 20 μg/ml tetracycline.

In the presence of HMP and HET co-feeding (0.54 g/liter, each), two fed-batch fermentations of TH115 resulted in an increase in thiamin production (210 mg/L at 48 hours, and 300 mg/L after 78 hours). The molar yields on substrates HMP or HET were 45% each at both 48 and 78 hours. Two other fermentations led to a slight decrease in thiamin production. Interestingly, higher thiamin excretion coincided with a severe growth-limiting event that occurred during the first hours of the fermentation, and which could be overcome by the addition of 25 g of nutrient broth (NB) and 1.6 mg of TPP to the 6-L cultivation. HPLC/DAD confirmed the presence of thiamin in the fermentation broth, and could be used to purify thiamin from the other UV-detectable compounds. Interestingly, neither HMP nor HET was detected by HPLC/DAD, indicating complete uptake of the co-feed applied at 0.54 g/liter. In any event, these results indicate that TH115 has a large capacity to synthesize TMP from exogenously-added precursors, dephosphorylate TMP to thiamin, and excrete thiamin into the culture medium. In addition, the ThiC coupling activity is apparently not rate limiting in this process.

EXAMPLE 7

Methods for Increasing Thiamin Compounds Production by Enhancing the Expression Level of Thiazole Biosynthetic Enzymes This example describes the construction of a DNA cassette containing the *B. subtilis* thiB operon containing genes tenAI-thiOSGFD, which can be used to overexpress said genes resulting in overproduction and excretion of thiamin products.

First, a thiazole auxotroph strain, deleted for the native promoter region in front of the tenAI-thiOSGFD operon, was generated. To do that, two DNA fragments (downstream TenA and upstream YjbQ fragments), located on each side of the promoter region, were first amplified from *B. subtilis* PY79 chromosome using primer pairs YjbQ+_BamHI (SEQ ID NO: 22)/YjbQ−_MluI (SEQ ID NO: 23) and TenA+_KpnI (SEQ ID NO: 24)/TenA−_XhoI (SEQ ID NO: 25). A third fragment, containing a chloramphenicol acetyltransferase cassette, was amplified from TH11 chromosomal DNA (PY79 ΔthiL::cat$_2$) using primers TenA-cat+_KpnI (SEQ ID NO: 26) and TenA-cat−_MluI (SEQ ID NO: 27). Assembling of these three fragments was then performed in pUC19 to generate plasmid pTH401, which contains the 'yjbQ$_3$'_MluI-$_3$cat$_5$-KpnI-$_5$tenA' DNA construction inserted between the PstI and EcoRI restriction sites. Transformation of plasmid pTH401 in TH95 and selection on Cm 5 μg/ml, yielded thiamin-, and thiazole-auxotroph TH403.

To construct a P$_{26}$ tenAI-thiOSGFD cassette, the cat cassette in pTH401 was excised by KpnI and MluI, and, then, was substituted by a PCR fragment containing the P$_{26}$ strong constitutive promoter, derived form the bacteriophage SPO1. This fragment was amplified from plasmid pUCSPO1-26 using primers P26+_MluI (SEQ ID NO: 28) and P26−_KpnI (SEQ ID NO: 29). Introduction of the thiB overexpressing cassette was then made by selecting for restoration of prototrophy in TH403 background. After transformation of the ligation mix creating the P$_{26}$ tenA' in-frame fusion into TH403, prototrophic transformants were selected for their ability to grow on minimal medium plates. Their chloramphenicol sensitivity and the presence of the P$_{26}$ promoter in front of the tenAI-thiOSGFD operon were confirmed. The resulting strain was named TH404 (FIG. 3).

Thiamin production with TH404 engineered strain was tested in 20-liter lab scale fermentors using standard fed-batch conditions (start volume: 6 liter) with HMP co-feeding (0.54 g/liter, w/w). Strain TH404 produced up to 315 mg/liter thiamin (Table 12). That number is significantly higher than the number obtained after 48 hours for strain TH95 (110 mg/liter, Table 9).

TABLE 12

Thiamin production of TH404 in 6-liter fermentation.

| Strain | OD$_{600}$ 48 hr | Thiamin products mg/L | | |
|---|---|---|---|---|
| | | Thiamin 48 hr | TMP 48 hr | TPP 48 hr |
| TH404 | 85 | 315 | 31 | 5 |

EXAMPLE 8

Methods for Increasing Thiamin Compounds Production by Enhancing the Expression Levels of both ThiA and Thiazole Biosynthetic Enzymes This example describes the combination of DNA cassettes containing the B. subtilis thiA gene and the B. subtilis thiB operon containing genes tenAI-thiOSGFD, which can be used to overexpress said gene resulting in overproduction and excretion of thiamin products.

In order to combine the B. subtilis P$_{26}$ tenAI-thiOSGFD cassette (described in Example 7) and the amplifiable P$_{26}$ thiA-cat cassette (described in Example 4), competent cells of strain TH404 were transformed with non-congressional concentration of chromosomal DNA extracted from strain TH116 using standard methods. Transformants were selected for resistance to 5 μg/ml chloramphenicol. PCR analysis confirmed that they contain the P$_{26}$ tenAI-thiOSGFD and P$_{26}$ thiA-cat cassettes. One Cm$^r$ colony, designated TH405, was saved for further studies. The expression of thiA in TH405 was increased by obtaining colonies that were resistant to successively higher levels of chloramphenicol. Specifically, a strain of TH405 resistant to 60 μg/ml chloramphenicol could be obtained. SDS-PAGE analysis of crude extracts of strain TH405 resistant to 60 μg/ml chloramphenicol showed a significantly higher level of ThiA protein than strain TH405 resistant to only 5 μg/ml, which is identical to the level obtained after amplification of the P$_{26}$ thiA-cat cassette in strain TH116 (Example 4).

Thiamin production with the TH405 engineered strain was tested in 20-liter lab scale fermentors using standard fed-batch conditions (start volume: 6 liter). Strain TH405 resistant to 60 μg/ml chloramphenicol produced between 34-37 mg/liter thiamin in 48 h (Table 13), which is a 6-fold increase in thiamin production compared to TH95 fermentation with 0.54 g/liter co-feed of HMP (Table 8). Thiamin production, however, was significantly lower than observed in co-feeding studies or with a strain overexpressing the thiB operon only (Table 12, Example 7). This result confirms our observation from Example 4, i.e. formation of HMP is rate-limiting, and that the putative missing gene that needs to be overexpressed in addition to thiA and the thiB operon, is not part of the thiB operon.

TABLE 13

Thiamin production of TH404 in 6-liter fermentation.

| Strain | OD$_{600}$ 24 hr | OD$_{600}$ 48 hr | Thiamin products (mg/L) | | | | | |
|---|---|---|---|---|---|---|---|---|
| | | | Thiamin 24 hr | TMP 24 hr | TPP 24 hr | Thiamin 48 hr | TMP 48 hr | TPP 48 hr |
| TH405 | 78 | 20 | 34 | 2 | 1 | 37 | 2 | 1 |

EXAMPLE 9

Methods for Increasing Thiamin Compounds Production by Increasing Glycine or Cysteine Availability This example describes experiments that increase thiamin production by growing thiamin-deregulated strains in the presence of glycine or cysteine, which are both precursors in the HET pathway.

Thiamin production with B. subtilis TH95 (tx26 tx1 ΔthiL) was tested in 6-liter lab scale fermentation using standard fed-batch conditions with HMP (0.54 g/liter) and glycine co-feeding (2 g/liter). Thiamin; TMP, and TPP production reached 14 mg/liter, 3 mg/liter, and 0.5 mg/liter, respectively, in 48 hours (Table 14), which is substantially higher than thiamin products levels in TH95 grown with just a HMP feed (Table 8).

Next, thiamin production with B. subtilis TH95 (tx26 tx1 ΔthiL) was tested in 6-liter lab scale fermentation using standard fed-batch conditions with HMP (0.54 g/liter) and cysteine co-feeding (0.5 g/liter); threonine (0.4 g/liter) and isoleucine (0.2 g/liter) were also added to facilitate cysteine assimilation. Thiamin production reached 8 mg/liter in 48 hours (Table 14), which is substantially higher than thiarnin titers in TH95 grown with just a HMP feed (Table 8).

Increasing thiamin production could also be achieved by addition of all four amino acids, glycine, cysteine, isoleucine, and threonine to the fermentation of TH95 (Table 14). Moreover increasing the expression of biosynthetic genes involved in the synthesis of these amino acids, or introducing mutations in regulatory genes or cis-acting regulatory sites that lead to increased expression of the said amino acid biosynthetic genes or by introducing mutations that lead to increased activity of said biosynthetic enzymes could increase thiamin productivity.

TABLE 14

Thiamin production of TH95 in 6-liter fermentation with the addition of glycine, cysteine-isoleucine-threonine, or glycine cysteine-isoleucine-threonine.

| Strain | Feed 60% Glucose plus | $OD_{600}$ 48 hr | Thiamin products (mg/L) | | |
|--------|----------------------|------------------|---------|-----|-----|
|        |                      |                  | Thiamin | TMP | TPP |
| TH95 | 0.54 g/L HMP, 2 g/L glycine | 65 | 14 | 3 | 0.5 |
| TH95 | 0.54 g/L HMP, 0.54 g/L L-cysteine, 0.4 g/L D,L-threonine, 0.2 g/L L-isoleucine | 60 | 8 | 2 | 0.5 |
| TH95 | 0.54 g/L HMP, 2 g/L glycine, 0.2 g/L L-cysteine, 0.4 g/L D,L-threonine, 0.2 g/L L-isoleucine | 75 | 11 | 2 | 0.4 |

EXAMPLE 10

Methods for Producing Thiamin Compounds Using Grewe Diamine as a Precursor

This example describes experiments demonstrating the production of thiamin by growing thiamin-deregulated strains in the presence of a derivative of HMP, 4-amino-2-methyl-5-pyrimidinemethaneamine (Grewe Diamine).

Grewe Diamine is a derivative of HMP in which the C-5 hydroxymethyl group is substituted by an aminomethyl group. Thiamin production with *B. subtilis* TH95 (tx26 tx1 ΔthiL) was tested in 6-liter lab scale fermentation using standard fed-batch conditions with Grewe Diamine and HET co-feeding (0.54 g/liter each). Thiamin production reached 53 mg/liter in 45.5 hours (Table 15). Increasing the level of Grewe Diamine in the feed solution to 2.7 g/liter increased thiamin production to 120 mg/liter in 46.5 hours (Table 15). These results demonstrate the feasibility of developing a fermentation process to produce thiamin from Grewe Diamine and HET. Moreover, these results demonstrate that *Bacillus subtilis* encodes one or more enzyme activities that can convert Grewe Diamine to HMP or a structurally similar compound that can then be used to produce thiamin.

TABLE 15

Thiamin production of TH95 in 6-liter fermentation with a Grewe Diamine and HET co-feed.

| Strain | Feed 60% Glucose plus | $OD_{600}$ 48 hr | Thiamin products (mg/L) | | |
|--------|----------------------|------------------|---------|-----|-----|
|        |                      |                  | Thiamin | TMP | TPP |
| TH95 | 0.54 g/L HET, 0.54 g/L Grewe Diamine | 44 | 53 | 7 | 1 |
| TH95 | 2.7 g/L HET, 2.7 g/L Grewe Diamine | 60 | 118 | 8 | 1 |

EXAMPLE 11

Isolated Genes and Mutations yloS/tx1

Strain Tx1 carries the tx1 mutation (see SEQ ID NO: 30 for a copy of the polynucleotide sequence having the mutation), which was isolated by screening thiA-lacZ fusion-containing bacteria for the Lac+ sphenotype in the presence of TPP. This strain (ΔthiL::cat4 amyE::thiA-lacZ tx1) was shown to be a strong thiamin bradytroph indicating that this mutation appeared to inactivate a residual TMP kinase activity or an unknown gene product involved in a secondary route that leads to the formation of TPP from thiamin. Reconstitution studies indicated that the Lac+ phenotype of Tx1 was not caused by a general defect in the thiazole or HMP pathways as judged by analysis of TH22 derivatives containing a block in either the HET (ΩthiF::pMUTIN) or HMP-P (ΩthiA::Tn917) pathways.

Strains with tx1 were confirmed to be bradytrophs based on their ability to grow in minimal medium supplemented with 2.5% nutrient broth, which does not contain any significant amounts of thiamin products. In these cultures, Tx1 produced approximately 10-fold more extracellular thiamin products than the control strain TH22 (ΩthiL::cat$_4$ ΩamyE::thiA-lacZ). Interestingly all the detectable thiamin produced was either in the form of thiamin or TPP; TMP was not detected in the culture medium. Genetic studies indicated that the thiamin bradytroph phenotype of Tx1 required ΔthiL::cat$_4$.

Genetic mapping studies using PBS1 generalized transduction under standard conditions showed that the tx1 mutation was not linked to either ΔthiL::cat$_4$ or ΩamyE::thiA-lacZ. However, tx1 showed 90% transduction linkage to zdi-82::Tn917 (BGSC#1A633) located at 140°. The transformation linkage to the same marker was 8%. Several Tn917-linked mutations located between 121° and 140° also showed significant linkage to tx1. One mutation, urc83::Tn917 (strain 1A611), showed high transduction linkage (>60%) and significant transformation linkage (10%). This insertion, which causes an auxotrophy for uracil+cysteine or uracil+methionine, is at the junction between the pyr operon and the cys operon (139°). A second mutation, yloA::Tn917 showed a similar linkage to tx1. Much higher transduction and DNA transformation linkage of tx1 to QspoVM::Tn917 mutation was observed suggesting that tx1 was allelic to yloS, which is adjacent to spoVM. The yloS gene shows weak amino acid similarity (P=0.23) to the TNR3 gene protein of *Schizosaccharomyces pombe*, which has been previously shown to have thiamin pyrophosphokinase activity. To determine if tx1 is allelic to yloS, a stable 448 bp long deletion mutation, starting at base 124 of the yloS gene (AyloS::cat$_4$) was constructed by PCR using standard methods and introduced into PY79. After introduction of ΩthiL::pMUTIN, the resulting double mutant was phenotypically similar to the original Tx1 mutant. Moreover, DNA sequencing of yloS in the Tx1 mutant revealed a single base mutation that resulted in a leucine-to-phenylalanine substitution at amino acid residue 116 (L116>F116; see SEQ ID NO: 31).

Based on these results, *B. subtilis* contains two biosynthetic routes to synthesize TPP from TMP: (1) direct enzymatic transformation of TMP to TPP by the product of thiL; and (2) enzymatic transformation of TMP to THI by an unknown phosphatase, followed by the pyrophosphorylation of THI to TPP by the product of yloS.

Route (1) has been shown to be present in Gram-negative organisms (e.g. *Salmonella typhimurium* and *E. coli*). Route (2) is present only in several Gram+ bacteria and some other eukaryotic microorganisms, including yeast (Llorente et al. (1999) Mol. Microbiol. 32:1140-1152). In addition, *B. subtilis* must contain a kinase activity that converts thiamin to TMP. This conclusion is based on genetic studies that showed that strain TH109 containing mutations AyloS::cat$_4$ and ΩthiA84::Tn917 could grow on minimal medium containing thiamin.

Protein database searches indicated that at least 13 bacterial genera contain one or more genes that encode a protein with significant homology to YloS: *Oceanobacillus, Listeria, Staphylococcus, Enterococcus, Streptococcus, Clostridium, Fusobacterium, Tropheryma, Mesorhizobium, Brucella, Thermotoga, Agrobacterium*, and *Helicobacter*. Most of these microorganisms are Gram$^+$ bacteria. Weaker homology to genes from non-bacterial organisms (e.g. yeast, *Drosophila melanogaster, Mus musailus*, and *Treponema pallidum*) was also detected. Interestingly, most of the yloS-containing bacterial species do not contain a thiL ortholog gene, and conversely most of the thiL-containing bacterial species do not contain a yloS ortholog (Table 16). This latter group consisted mostly of Gram-negative genera. Like *B. subtilis*, *Oceanobacillus iheyensis* contains both genes. These results indicate that eubacteria can be classified into two groups depending on the ability to form TPP by pyrophosphorylation of thiamin or by phosphorylation of TMP. Moreover, many of the Gram$^+$ bacteria that contain only a yloS ortholog and not a thiL ortholog are known pathogens, suggesting the yloS gene could be used as a target for developing anti-bacterial agents.

TABLE 16

Presence or absence of yloS and thiL orthologs in various bacterial genera.

| Microorganism | yloS ortholog | thiL ortholog |
|---|---|---|
| Bacillus subtilis 168 | Yes | Yes |
| Oceanobacillus iheyensis HTE831 | Yes | Yes |
| Bacillus stearothermophilus | Yes | No |
| Listeria monocytogenes EGD-e | Yes | No |
| Staphylococcus aureus | Yes | No |
| Enterococcus faecalis V583 | Yes | No |
| Enterococcus faecium | Yes | No |
| Streptococcus pneumoniae TIGR4 and R6 | Yes | No |
| Streptococcus pyogenes | Yes | No |
| Clostridium acetobutylicum ATCC-824D | Yes | No |
| Clostridium tetani E88 | Yes | No |
| Clostridium perfringens str.13 | Yes | No |
| Listeria monocytogenes EGD-e | Yes | No |
| Escherichia coli K12 | No | Yes |
| Escherichia coli O157: H7 EDL933 | No | Yes |
| Shigella flexneri 2a str. 301 | No | Yes |
| Haemophilus influenzae Rd | No | Yes |
| Salmonella typhimurium LT2 | No | Yes | yuaJ/tx26-1

PBS1 generalized transduction experiments, using standard conditions, showed that the Tx26 mutant contained two mutations located at different regions of the chromosome. In these experiments, phage lysates were first prepared on standard wild-type *B. subtilis* strains containing a phenotypically-silent Tn917 insertion located around the chromosome (*Bacillus* Genetic Stock Center). Two of these lysates, one carrying ΩyufR::Tn917 (BGSC# 1A642) at map position 2770 and the other carrying ΩmotA::Tn917 (BGSC#1A631) at map position 122.5°, were able to revert the Tx26 phenotype to wild type (reversion of Lac$^+$ to Lac$^-$ on minimal medium containing 1 μM TPP and reversion of pyrithiamine-resistance to pyrithiamine-sensitivity using 0.1 μM pyrithiamine). These unexpected results indicated that both mutations are required for the thiamin-deregulation phenotype exhibited by Tx26. One mutation, designated tx26-1, showed 70% linkage to ΩyufR::Tn917, and the other mutation, designated tx26-2, showed 59% linkage to ΩmotA::Tn917. Moreover, in back-cross experiments, the pyrithiamine-resistance marker of Tx26 could be transferred into sensitive *B. subtilis* strains by congression DNA transformation. These pyrithiamine-resistant transformants were also thiamin-deregulated (Lac$^+$ on minimal medium containing 1 μM TPP and resistant to 0.1 μM pyrithiamine).

Three-factor cross experiments using donor strains containing different combinations of antibiotic insertions in yufR/maeN (277.1°), yuiGH (281°), yurI (285.6°), gerAB and yvaC (294°) further mapped the tx26-1 mutation close to yuaJ, a thiamin-regulated gene, which was identified using microarray analysis (see below). To determine if tx26-1 is allelic to yuaJ, a deletion mutation of yuaJ was first constructed using standard PCR methods. To achieve this, a 324 bp-long internal fragment of yuaJ starting at position 353 was PCR-amplified and inserted between the BamHI and HindIII sites of pMUTIN2 using primers BsyuaJ/for/Hind3 (SEQ ID NO: 16) and BsyuaJ/rev/Bam (SEQ ID NO: 17), creating plasmid pTH31. As expected, introduction of ΩyuaJ::pMUTIN into wild type strains, (e.g. PY79) or thiA mutants were without phenotype. However, in several genetic crosses, the ΩyuaJ::pMUTIN2 disruption showed very high transduction and transformation linkages (100%) to tx26-1. These linkage results placed tx26-1 within or near yuaJ. Moreover, transduction and transformation of ΩyuaJ::pMUTIN into strain TH112 (tx26-1 tx26-2 ΔthiL), resulted in Erm$^r$ colonies that were resistant to 0.1 μM pyrithiamine. Finally, DNA sequence analysis of yuaJ from Tx26 confirmed that tx26-1 (see SEQ ID NO: 33 for a copy of the polynucleotide sequence containing the mutation) was an allele of yuaJ. Comparison of DNA sequences from four independent PCR fragments from Tx26 and two from the wild type parent strain (PY79) detected a single base mutation that resulted in the change of a glutamine residue at amino acid position 35 to an Ocher stop codon (Q35 (CAA)>Stop (TAA); see SEQ ID NO: 34 in comparison to the amino acid sequence ID NO: 35 of the wild type YuaJ). Protein database searches indicated that yuaJ encodes a thiamin permease or a regulator of surface antigen protein genes. Hydrophobicity analysis indicated that YuaJ contains six membrane-spanning domains. Introduction of the tx26-1 mutation is predicted to produce a truncated 35 amino acid protein, which is likely to undergo proteolysis. These results, together with the genetic data presented above, suggest that loss-of-function of yuaJ is responsible for the thiamin-deregulation phenotype. Moreover, microarray data (see below) indicated that expression of yuaJ is regulated by TPP and inspection of the predicted 5' leader region revealed a DNA sequence with strong homology to the consensus THI box regulatory sequence.

tx26-2

Generalized transduction mapping studies (two-factor crosses), using a collection of PBS1 phage lysates prepared on strains containing Tn917 insertions, showed 60% linkage of tx26-2 to ΩmotA::Tn917 (BGSC#1A631) located at 122.5° on the *B. subtilis* genome. This genetic map position corresponded to a cluster of genes, ykoFEDC, whose transcript levels were shown to increase in microarray studies of the thiamin deregulated Tx26 strain (see Table 17). Moreover, these genes appeared to be organized as an operon and contain a THI box regulatory elements in the promoter region upstream of ykoF. DNA sequencing of this operon, including a 400 bp region upstream of ykoF, detected a single base mutation in the ykoD gene that resulted in a Asp$_{180}$ (GAC) to Asn$_{180}$ (AAC) substitution (see SEQ ID NO: 37 for the amino acid sequence in comparison to amino acid sequence ID NO: 38 of the wild type YkoD). Protein database searches indicated that ykod encodes a HMP transport ATP-binding protein. Two other genes in this operon, ykoE and C, are predicted to encode HMP transport permeases. These results indicated that the tx26-2 mutation is an allele of ykod and affect cellular transport of thiamin (see SEQ ID NO: 36 for a copy of the polynucleotide sequence containing the mutation).

Thiamin-Regulated Genes Identified Through Microarray Profiling

In order to perform microarray profiling, PY79 was grown in shake-flask cultures that contained 50 ml Spizizen minimal medium with or without added thiamin pyrophosphate. Overnight cultures were diluted to Klett=10 units into fresh medium and grown to exponential growth phase (Klett=100 units). Cells from half of the culture were collected by centrifugation, and the total RNA was immediately extracted as previously described (Lee et al. (2001) *J. Bacteriol.* 183: 7371-7380). The remaining culture was grown to early stationary phase before RNA extraction. Early stationary phase was judged to be 30 min after glucose exhaustion; glucose content in the medium was measured by a glucose analyzer 2 (Beckman, Fullerton, Calif.) using standard procedures. Preparation of labeled cDNA targets, microarray hybridization and staining procedures, and data analysis are described in Lee et al. above.

In addition to known thiamin-regulated *B. subtilis* genes thiA and tenAI-thiOSGFD, analysis of the results also showed a 3-fold or higher transcript level of several other genes in cells grown in the absence of TPP. These genes are listed in Table 17. These results were confirmed by comparison of microarray data of wild-type and thiamin-deregulated (Tx26) strains grown in minimal medium in the presence of TPP. Moreover, in several of these genes, a consensus cis-acting regulatory site (thi box) could be visualized within the 5' leader region, confirming regulation by TPP. It can be anticipated that increasing or decreasing the expression of these genes individually or in concert together, or in combination with known biosynthetic genes, could also lead to higher thiamin, HMP and/or thiazole production.

TABLE 17

Change in transcript levels of genes in *B. subtilis* in response to TPP[a].

| Gene | Enzyme/Function | wt$^-$vit/ wt$^+$vit | deg$^+$vit/ wt$^+$vit |
|---|---|---|---|
| thiA | Biosynthesis of hydroxymethylpyrimidine phosphate | 62 | 22 |
| thiK | Hydroxyethylthiazole kinase | n/c | 4.7 |
| thiC | Thiamin phosphate pyrophosphorylase | n/c | 2.4 |
| thiO (goxB) | Glycine oxidase | 67 | 19 |
| thiS (yjbS) | Biosynthesis of hydroxyethylthiazole phosphate | 84 | 33 |
| thiG (yjbT) | Biosynthesis of hydroxyethylthiazole phosphate | 82 | 13 |
| thiF (yjbU) | Biosynthesis of hydroxyethylthiazole phosphate | 90 | 11 |
| thiD1 (yjbV) | Possible phosphomethylpyrimidine kinase | 32 | 14 |
| thiD2 | Possible phosphomethylpyrimidine kinase | n/c[b] | n/c |
| thiL (ydiA) | Unknown/possible thiL ortholog (TMP kinase) | n/c | n/c |
| ytbJ | Unknown/possible thiI ortholog (sulfur transferase) | n/c | n/c |
| dxs (yqiE) | 1-deoxy-D-xylulose synthase | n/c | n/c |
| ykoC | Unknown; similar to unknown proteins | 12 | 4 |
| ykoD | Unknown; similar to cation ABC transporter | 26 | 5 |
| ykoE | Unknown | 17 | 32 |
| ykoF | Unknown | 20 | 5 |
| yloS | Thiamin pyrophosphorylase | 1.6 | 0.3 |
| yuaA | Thiamin permease | 7.4 | 5.3 |
| ylmB | Unknown; similar to acetylornithine deacetylase | 5.0 | 7.6 |

[a]Transcript ratios were calculated by dividing the average difference values (after normalization) from hybridization experiments of wild-type cells grown to exponential phase in minimal medium without TPP treatment by those with TPP treatment (wt$^-$/wt$^+$) or from hybridization experiments of deregulated mutant Tx26 cells grown to exponential phase in minimal medium with vitamin treatment (vit) by those of wild-type cells grown under the same condition(deg$^+$/wt$^+$). For some genes (in bold), average difference values were obtained from duplicate probe sets per hybridization experiment.
[b]n/c, no change in average difference values.

The invention claimed is:

1. A microorganism of the genus *Bacillus*, which is *Bacillus subtilis* TH95 (ATCC PTA-5221).

2. A microorganism of the genus *Bacillus*, which is selected from the group consisting of *Bacillus subtilis* TH116 (ATCC PTA-5224), TH115 (ATCC PTA-5223), TH404 (DSM 16333) and TH405 (DSM 16334).

3. A microorganism of the genus *Bacillus*, which is *Bacillus subtilis* TH101 (ATCC PTA-5222).

4. A microorganism of the genus *Bacillus*, the microorganism containing a mutation that deregulates thiamin production and causes thiamin products to be released into a culture media, and wherein the mutation is selected from the group consisting of a mutation in ydiA/thiL and orthologs thereof (a ΔthiL mutation), a mutation in yloS and orthologs thereof (a tx1 mutation), and a mutation in yuaJ and orthologs thereof and in ykoD and orthologs thereof (a tx26 mutation), and combinations thereof, wherein the mutation is selected from the group consisting of:
   (a) deletion of the thiL gene encoding thiamin monophosphate kinase,
   (b) mutation in the yloS gene encoding thiamin pyrophosphorylase, said mutation leading to a leucine to phenylalanine substitution at the amino acid residue corresponding to position 116 in the respective *Bacillus subtilis* wild-type YloS sequence, and
   (c) loss-of-function mutation in the yuaJ gene encoding thiamin permease, and mutation in the ykoD gene encoding thiamin-related ABC transporter, said mutation leading to an aspartic acid to asparagine substitution at the amino acid residue corresponding to position 180 in the respective *Bacillus subtilis* wild-type YkoD sequence.

5. An isolated polynucleotide sequence comprising a tx1 mutation, wherein the sequence is SEQ ID NO:30 or a polynucleotide sequence that hybridizes to the complement of SEQ ID NO: 30 under stringent conditions comprising hybridization in a buffer of 40% formamide, 1 M NaCl, 1% sodium dodecyl sulfate (SDS) at 37° C., and at least one wash in 0.2×SSC at a temperature of 55° C. for 20 minutes, and, when the polynucleotide is present in a microorganism, it causes a deregulation of thiamin production.

6. An isolated polynucleotide sequence comprising a first mutation with 70% linkage to ΔyufR::Tn917 (tx26-1) and a second mutation with 59% linkage to ΩmotA::Tn917 (tx26-2), wherein the presence of both of the mutations in a thiamin-producing microorganism causes a deregulation of thiamin production, and wherein the tx26-1 mutation is present in a polynucleotide sequence set forth in SEQ ID NO: 33 or a polynucleotide sequence that hybridizes to the complement of SEQ ID NO: 33 under stringent conditions comprising hybridization in a buffer of 40% formamide, 1M NaCl, 1% sodium dodecyl sulfate (SDS) at 37° C., and at least one wash in 0.2×SSC at a temperature of 55° C. for 20 minutes, and wherein the tx26-2 mutation is present in a polynucleotide sequence set forth in SEQ ID NO: 36 or a polynucleotide sequence that hybridizes to the complement of SEQ ID NO: 36 under stringent conditions comprising hybridization in a buffer of 40% formamide, 1M NaCl, 1% sodium dodecyl sulfate (SDS) at 37° C., and at least one wash in 0.2×SSC at a temperature of 55° C. for 20 minutes, and, when the polynucleotide sequence comprising the tx26-1 and tx26-2 mutations is present in a microorganism, it causes a deregulation of thiamin production.

* * * * *

SEQUENCE LISTING

```
<160> NUMBER OF SEQ ID NOS: 38

<210> SEQ ID NO 1
<211> LENGTH: 29
<212> TYPE: DNA
<213> ORGANISM: Artificial
<220> FEATURE:
<223> OTHER INFORMATION: PCR primer

<400> SEQUENCE: 1
atgccatatg caaaacaatt cagtgcagc                                    29

<210> SEQ ID NO 2
<211> LENGTH: 36
<212> TYPE: DNA
<213> ORGANISM: Artificial
<220> FEATURE:
<223> OTHER INFORMATION: PCR primer

<400> SEQUENCE: 2
gcatggatcc tcattattga tataaattgc ttcccg                            36
```

<210> SEQ ID NO 3
<211> LENGTH: 32
<212> TYPE: DNA
<213> ORGANISM: Artificial
<220> FEATURE:
<223> OTHER INFORMATION: PCR primer

<400> SEQUENCE: 3
acgtgtttaa acgcaggttg ttctcaatgt cg					32

<210> SEQ ID NO 4
<211> LENGTH: 33
<212> TYPE: DNA
<213> ORGANISM: Artificial
<220> FEATURE:
<223> OTHER INFORMATION: PCR primer

<400> SEQUENCE: 4
acgtgcggcc gcgatcaatt ttgaactctc tcc					33

<210> SEQ ID NO 5
<211> LENGTH: 27
<212> TYPE: DNA
<213> ORGANISM: Artificial
<220> FEATURE:
<223> OTHER INFORMATION: PCR primer

<400> SEQUENCE: 5
atgccatatg gatgcacaat cagcagc					27

<210> SEQ ID NO 6
<211> LENGTH: 36
<212> TYPE: DNA
<213> ORGANISM: Artificial
<220> FEATURE:
<223> OTHER INFORMATION: PCR primer

<400> SEQUENCE: 6
gcatcccggg tcagtctgaa aaccttgatg gacagc					36

<210> SEQ ID NO 7
<211> LENGTH: 31
<212> TYPE: DNA
<213> ORGANISM: Artificial
<220> FEATURE:
<223> OTHER INFORMATION: PCR primer

<400> SEQUENCE: 7
gggaagcttt gcggtacctt caaaatggac t					31

<210> SEQ ID NO 8
<211> LENGTH: 29
<212> TYPE: DNA
<213> ORGANISM: Artificial
<220> FEATURE:
<223> OTHER INFORMATION: PCR primer

<400> SEQUENCE: 8
gggggatcca atctgccgac gcttactct					29

<210> SEQ ID NO 9
<211> LENGTH: 28
<212> TYPE: DNA
<213> ORGANISM: Artificial
<220> FEATURE:
<223> OTHER INFORMATION: PCR primer

```
<400> SEQUENCE: 9
gggggtaccg aaaattggat aaagtggg                                       28

<210> SEQ ID NO 10
<211> LENGTH: 29
<212> TYPE: DNA
<213> ORGANISM: Artificial
<220> FEATURE:
<223> OTHER INFORMATION: PCR primer

<400> SEQUENCE: 10
gggacgcgtt caactaacgg ggcaggtta                                      29

<210> SEQ ID NO 11
<211> LENGTH: 33
<212> TYPE: DNA
<213> ORGANISM: Artificial
<220> FEATURE:
<223> OTHER INFORMATION: PCR primer

<400> SEQUENCE: 11
gggacgcgta agtacagtcg gcattatctc ata                                 33

<210> SEQ ID NO 12
<211> LENGTH: 23
<212> TYPE: DNA
<213> ORGANISM: Artificial
<220> FEATURE:
<223> OTHER INFORMATION: PCR primer

<400> SEQUENCE: 12
atgcggatcc cgtccggacc gcc                                            23

<210> SEQ ID NO 13
<211> LENGTH: 25
<212> TYPE: DNA
<213> ORGANISM: Artificial
<220> FEATURE:
<223> OTHER INFORMATION: PCR primer

<400> SEQUENCE: 13
cgatcccggg gcctcccatc gcggc                                          25

<210> SEQ ID NO 14
<211> LENGTH: 33
<212> TYPE: DNA
<213> ORGANISM: Artificial
<220> FEATURE:
<223> OTHER INFORMATION: PCR primer

<400> SEQUENCE: 14
atgccccggg atttgcctaa gcttcatcct aac                                 33

<210> SEQ ID NO 15
<211> LENGTH: 29
<212> TYPE: DNA
<213> ORGANISM: Artificial
<220> FEATURE:
<223> OTHER INFORMATION: PCR primer

<400> SEQUENCE: 15
cgatgaattc agcccttctg caaaacctt                                      29

<210> SEQ ID NO 16
<211> LENGTH: 33
<212> TYPE: DNA
```

<213> ORGANISM: Artificial
<220> FEATURE:
<223> OTHER INFORMATION: PCR primer

<400> SEQUENCE: 16
agctaagctt ggcagccgtt attttagaca ttg                    33

<210> SEQ ID NO 17
<211> LENGTH: 34
<212> TYPE: DNA
<213> ORGANISM: Artificial
<220> FEATURE:
<223> OTHER INFORMATION: PCR primer

<400> SEQUENCE: 17
tgcaggatcc ataaaaactg cgctgaccac tgaa                   34

<210> SEQ ID NO 18
<211> LENGTH: 24
<212> TYPE: DNA
<213> ORGANISM: Artificial
<220> FEATURE:
<223> OTHER INFORMATION: PCR primer

<400> SEQUENCE: 18
gagagaattc gctgaaagga cagc                              24

<210> SEQ ID NO 19
<211> LENGTH: 35
<212> TYPE: DNA
<213> ORGANISM: Artificial
<220> FEATURE:
<223> OTHER INFORMATION: PCR primer

<400> SEQUENCE: 19
tctcggatcc ttagatcaat ttcccttcaa atacg                  35

<210> SEQ ID NO 20
<211> LENGTH: 26
<212> TYPE: DNA
<213> ORGANISM: Artificial
<220> FEATURE:
<223> OTHER INFORMATION: PCR primer

<400> SEQUENCE: 20
gagaggatcc atcgttgaca ttatcc                            26

<210> SEQ ID NO 21
<211> LENGTH: 27
<212> TYPE: DNA
<213> ORGANISM: Artificial
<220> FEATURE:
<223> OTHER INFORMATION: PCR primer

<400> SEQUENCE: 21
ctctctgcag ctttctaaca ctgtctg                           27

<210> SEQ ID NO 22
<211> LENGTH: 30
<212> TYPE: DNA
<213> ORGANISM: Artificial
<220> FEATURE:
<223> OTHER INFORMATION: PCR primer

<400> SEQUENCE: 22
atcaggatcc cgctcctgct gcttgcgctg                        30

<210> SEQ ID NO 23
<211> LENGTH: 53
<212> TYPE: DNA
<213> ORGANISM: Artificial
<220> FEATURE:
<223> OTHER INFORMATION: PCR primer

<400> SEQUENCE: 23
tatgagataa tgccgactgt acttacgcgt ccttatttgg tcaagattta tcc     53

<210> SEQ ID NO 24
<211> LENGTH: 64
<212> TYPE: DNA
<213> ORGANISM: Artificial
<220> FEATURE:
<223> OTHER INFORMATION: PCR primer

<400> SEQUENCE: 24
cccactttat ccaattttcg ggtacctaag gaggtaactc atatgatttg tgaagttttc     60
agaa     64

<210> SEQ ID NO 25
<211> LENGTH: 31
<212> TYPE: DNA
<213> ORGANISM: Artificial
<220> FEATURE:
<223> OTHER INFORMATION: PCR primer

<400> SEQUENCE: 25
ctgctcgagc cagccttctt ttcgataggc c     31

<210> SEQ ID NO 26
<211> LENGTH: 64
<212> TYPE: DNA
<213> ORGANISM: Artificial
<220> FEATURE:
<223> OTHER INFORMATION: PCR primer

<400> SEQUENCE: 26
cttctgaaaa cttcacaaat catatgagtt acctccttag gtacccgaaa attggataaa     60
gtgg     64

<210> SEQ ID NO 27
<211> LENGTH: 53
<212> TYPE: DNA
<213> ORGANISM: Artificial
<220> FEATURE:
<223> OTHER INFORMATION: PCR primer

<400> SEQUENCE: 27
ggataaatct tgaccaaata aggacgcgta agtacagtcg gcattatctc ata     53

<210> SEQ ID NO 28
<211> LENGTH: 33
<212> TYPE: DNA
<213> ORGANISM: Artificial
<220> FEATURE:
<223> OTHER INFORMATION: PCR primer

<400> SEQUENCE: 28
gggttacgcg tggccgctaa ctacactaac agc     33

<210> SEQ ID NO 29
<211> LENGTH: 31
<212> TYPE: DNA

<213> ORGANISM: Artificial
<220> FEATURE:
<223> OTHER INFORMATION: PCR primer

<400> SEQUENCE: 29
gggttggtac ctttaattct cgagtgttaa g                            31

<210> SEQ ID NO 30
<211> LENGTH: 642
<212> TYPE: DNA
<213> ORGANISM: Bacillus subtilis
<220> FEATURE:
<221> NAME/KEY: mutation
<222> LOCATION: (346)..(346)
<223> OTHER INFORMATION: Mutation tx1 in ylos gene

<400> SEQUENCE: 30

```
atgaaaacaa ttaatatcgt tgcgggaggc ccgaaaaatc tcattcccga tctaaccggc    60
tatacggatg aacacacgct ttggatcggt gttgacaaag gcaccgtcac tctcttagat   120
gccgggatca ttcctgttga agccttcgga gatttgaca gcataacgga gcaagaacgc   180
cggcgaatag aaaaagccgc tcccgccctt catgtgtatc aagcagaaaa agatcaaaca   240
gatttagacc tcgcccttga ttgggcgctg aaaagcagc cggatattat tcagattttc   300
ggcattacag gcggcagagc tgatcatttt ttaggaaaca ttcagtttct gtataaaggt   360
gtaaaaacga acataaaaat taggctgata gacaaacaaa atcatattca aatgttccct   420
cctggtgaat atgatattga gaaggatgaa aataagcgat atatctcctt catacccgttt   480
tccgaagaca tacatgagct gaccctgacc ggttttaaat atcctctaaa taattgtcat   540
attacgctcg gttcaacact atgtattagt aacgaactca ttcattcacg aggtactttt   600
tcgtttgcaa aaggcatatt aataatgata agaagcacgg at                     642
```

<210> SEQ ID NO 31
<211> LENGTH: 214
<212> TYPE: PRT
<213> ORGANISM: Bacillus subtilis

<400> SEQUENCE: 31

Met Lys Thr Ile Asn Ile Val Ala Gly Gly Pro Lys Asn Leu Ile Pro
1               5                   10                  15

Asp Leu Thr Gly Tyr Thr Asp Glu His Thr Leu Trp Ile Gly Val Asp
            20                  25                  30

Lys Gly Thr Val Thr Leu Leu Asp Ala Gly Ile Ile Pro Val Glu Ala
        35                  40                  45

Phe Gly Asp Phe Asp Ser Ile Thr Glu Gln Glu Arg Arg Arg Ile Glu
    50                  55                  60

Lys Ala Ala Pro Ala Leu His Val Tyr Gln Ala Glu Lys Asp Gln Thr
65                  70                  75                  80

Asp Leu Asp Leu Ala Leu Asp Trp Ala Leu Glu Lys Gln Pro Asp Ile
                85                  90                  95

Ile Gln Ile Phe Gly Ile Thr Gly Gly Arg Ala Asp His Phe Leu Gly
            100                 105                 110

Asn Ile Gln Phe Leu Tyr Lys Gly Val Lys Thr Asn Ile Lys Ile Arg
        115                 120                 125

Leu Ile Asp Lys Gln Asn His Ile Gln Met Phe Pro Pro Gly Glu Tyr
    130                 135                 140

Asp Ile Glu Lys Asp Glu Asn Lys Arg Tyr Ile Ser Phe Ile Pro Phe
145                 150                 155                 160

Ser Glu Asp Ile His Glu Leu Thr Leu Thr Gly Phe Lys Tyr Pro Leu
            165                 170                 175

Asn Asn Cys His Ile Thr Leu Gly Ser Thr Leu Cys Ile Ser Asn Glu
            180                 185                 190

Leu Ile His Ser Arg Gly Thr Phe Ser Phe Ala Lys Gly Ile Leu Ile
        195                 200                 205

Met Ile Arg Ser Thr Asp
    210

<210> SEQ ID NO 32
<211> LENGTH: 214
<212> TYPE: PRT
<213> ORGANISM: Bacillus subtilis

<400> SEQUENCE: 32

Met Lys Thr Ile Asn Ile Val Ala Gly Gly Pro Lys Asn Leu Ile Pro
1               5                   10                  15

Asp Leu Thr Gly Tyr Thr Asp Glu His Thr Leu Trp Ile Gly Val Asp
            20                  25                  30

Lys Gly Thr Val Thr Leu Leu Asp Ala Gly Ile Ile Pro Val Glu Ala
        35                  40                  45

Phe Gly Asp Phe Asp Ser Ile Thr Glu Gln Glu Arg Arg Ile Glu
    50                  55                  60

Lys Ala Ala Pro Ala Leu His Val Tyr Gln Ala Glu Lys Asp Gln Thr
65                  70                  75                  80

Asp Leu Asp Leu Ala Leu Asp Trp Ala Leu Lys Gln Pro Asp Ile
            85                  90                  95

Ile Gln Ile Phe Gly Ile Thr Gly Gly Arg Ala Asp His Phe Leu Gly
            100                 105                 110

Asn Ile Gln Leu Leu Tyr Lys Gly Val Lys Thr Asn Ile Lys Ile Arg
        115                 120                 125

Leu Ile Asp Lys Gln Asn His Ile Gln Met Phe Pro Pro Gly Glu Tyr
    130                 135                 140

Asp Ile Glu Lys Asp Glu Asn Lys Arg Tyr Ile Ser Phe Ile Pro Phe
145                 150                 155                 160

Ser Glu Asp Ile His Glu Leu Thr Leu Thr Gly Phe Lys Tyr Pro Leu
            165                 170                 175

Asn Asn Cys His Ile Thr Leu Gly Ser Thr Leu Cys Ile Ser Asn Glu
            180                 185                 190

Leu Ile His Ser Arg Gly Thr Phe Ser Phe Ala Lys Gly Ile Leu Ile
        195                 200                 205

Met Ile Arg Ser Thr Asp
    210

<210> SEQ ID NO 33
<211> LENGTH: 576
<212> TYPE: DNA
<213> ORGANISM: Bacillus subtilis
<220> FEATURE:
<221> NAME/KEY: mutation
<222> LOCATION: (103)..(103)
<223> OTHER INFORMATION: Mutation tx26-1 in yuaJ

<400> SEQUENCE: 33
atgaatcaat ctaagcaact ggttcgcctt attgaaattg ccattatgac agcggcagcc      60
gttattttag acattgtctc aggaatgttt cttagcatgc cttaaggagg ctcggtctcc     120
atcatgatga ttccgatctt tttaatttcg tttcgctggg gtgtcaaagc aggtcttact     180

-continued

```
acaggtttgt tgacaggtct agtacaaata gcaatcggaa acttgtttgc tcaacatcct    240
gtacagctat tgttagatta cattgtcgct ttcgcagcaa tcggcataag cggctgtttc    300
gcttcttctg tccgtaaagc cgctgtatca aaaacaaaag ggaaattgat tgtttcagtg    360
gtcagcgcag ttttatcgg cagtttgctg cgctatgccg cgcatgtcat ttcaggagct    420 gtgttttcg gcagctttgc tccaaaagga acaccggtat ggatttattc tttaacttat    480
aatgcgactt acatggttcc ttcattcatt atttgtgcaa ttgtcctatg tttattattt    540
atgacagcac cccgtctgct aaaagtgac aaagcg                              576
```

<210> SEQ ID NO 34
<211> LENGTH: 34
<212> TYPE: PRT
<213> ORGANISM: Bacillus subtilis

<400> SEQUENCE: 34

Met Asn Gln Ser Lys Gln Leu Val Arg Leu Ile Glu Ile Ala Ile Met
1               5                   10                  15

Thr Ala Ala Ala Val Ile Leu Asp Ile Val Ser Gly Met Phe Leu Ser
            20                  25                  30

Met Pro

<210> SEQ ID NO 35
<211> LENGTH: 192
<212> TYPE: PRT
<213> ORGANISM: Bacillus subtilis

<400> SEQUENCE: 35

Met Asn Gln Ser Lys Gln Leu Val Arg Leu Ile Glu Ile Ala Ile Met
1               5                   10                  15

Thr Ala Ala Ala Val Ile Leu Asp Ile Val Ser Gly Met Phe Leu Ser
            20                  25                  30

Met Pro Gln Gly Gly Ser Val Ser Ile Met Met Ile Pro Ile Phe Leu
        35                  40                  45

Ile Ser Phe Arg Trp Gly Val Lys Ala Gly Leu Thr Thr Gly Leu Leu
    50                  55                  60

Thr Gly Leu Val Gln Ile Ala Ile Gly Asn Leu Phe Ala Gln His Pro
65                  70                  75                  80

Val Gln Leu Leu Leu Asp Tyr Ile Val Ala Phe Ala Ile Gly Ile
                85                  90                  95

Ser Gly Cys Phe Ala Ser Ser Val Arg Lys Ala Val Ser Lys Thr
            100                 105                 110

Lys Gly Lys Leu Ile Val Ser Val Ser Ala Val Phe Ile Gly Ser
        115                 120                 125

Leu Leu Arg Tyr Ala Ala His Val Ile Ser Gly Ala Val Phe Phe Gly
    130                 135                 140

Ser Phe Ala Pro Lys Gly Thr Pro Val Trp Ile Tyr Ser Leu Thr Tyr
145                 150                 155                 160

Asn Ala Thr Tyr Met Val Pro Ser Phe Ile Cys Ala Ile Val Leu
                165                 170                 175

Cys Leu Leu Phe Met Thr Ala Pro Arg Leu Leu Lys Ser Asp Lys Ala
            180                 185                 190

<210> SEQ ID NO 36
<211> LENGTH: 1470
<212> TYPE: DNA
<213> ORGANISM: Bacillus subtilis
<220> FEATURE:

```
<221> NAME/KEY: mutation
<222> LOCATION: (538)..(538)
<223> OTHER INFORMATION: Mutation tx26-2 in ykoD

<400> SEQUENCE: 36
atgcaagcct tgatgagct tctgacggtt gagcagctca gcttctctta tgaagaagac      60
gagaaaccgg tttttcaaga catttcgttt gagcttcaaa aaggagaatg tgttttatta     120
ttaggaccga gcggatgcgg taaaagctcg ctcgcccttt gtttaaacgg tctatatccg     180
gaggcttgcg acggcattca gtccggacat gtatttctat ttcaaaagcc ggtcacagat     240
gctgaaacct ccgaaacgat tactcagcat gccggggtcg ttttcagga tcctgatcag     300
cagttctgca tgctgacggt ggaggacgaa atagcgttcg ggctggaaaa tctgcaaatt     360
ccaaaagaag aaatgacaga gaaaatcaac gccgtattag aaaaattacg cattacccat     420
ttaaaagaaa aaatgatctc aaccctttca ggaggacaaa agcagaaagt ggctctcgcc     480
tgtatttttgg cgatggagcc tgagcttatt attttagatg agccgacctc tcttttaaac     540
cctttctcag ctcggggagtt cgttcatctg atgaaggatc ttcagcggga aaaaggtttc     600
agcctcctcg tcattgagca ccagcttgat gaatgggcgc cttggattga gaaacgatc     660
gtactcgaca aatcaggcaa aaaggcactg gatggcctga cgaaaaatct atttcagcat     720
gaagcggaga cactaaagaa attgggcatc gcaattccaa aggtctgtca tctgcaggaa     780
aagctgagta tgccgtttac tttatcaaaa gagatgctgt tcaaagagcc tattcctgcc     840
gggcatgtca aaagaagaa agccccttct gggggagagtg tgcttgaagt cagcagcctt     900
tcgttcgcga gaggacagca ggcgattttc aaagacatca gcttttcgtt gcgcgaaggc     960
tctttaacgg cgcttgtcgg tccgaacgga actggaaaat cgacgctcct atcagttctg    1020
gccagtctca tgaaaccgca aagcggcaaa atccttctct atgatcagcc gctgcagaaa    1080
tataaagaaa aagaattgcg taaacggatg ggatttgttt ttcaaaaccc tgagcatcaa    1140
ttcgtcaccg atacggtgta tgacgagctt ctgttcggcc agaaagcaaa tgctgaaact    1200
gagaaaaaag cgcaacacct gctgcagcgt tttggtcttg cgcatttggc tgatcatcat    1260
ccgtttgcga tcagccaagg gcaaaaacgg cgactgagcg tagctactat gctcatgcat    1320
gacgtaaagg ttttattatt agacgaacca acctttggcc aggatgcccg cacggcggct    1380
gaatgcatgg aaatgattca acgtatcaag gcagagggaa ctgctgtcct tatgattaca    1440
caaggatatg gagcaagtct cttcgtatgc                                     1470

<210> SEQ ID NO 37
<211> LENGTH: 490
<212> TYPE: PRT
<213> ORGANISM: Bacillus subtilis

<400> SEQUENCE: 37

Met Gln Ala Phe Asp Glu Leu Leu Thr Val Glu Gln Leu Ser Phe Ser
1               5                   10                  15

Tyr Glu Glu Asp Glu Lys Pro Val Phe Gln Asp Ile Ser Phe Glu Leu
                20                  25                  30

Gln Lys Gly Glu Cys Val Leu Leu Gly Pro Ser Gly Cys Gly Lys
            35                  40                  45

Ser Ser Leu Ala Leu Cys Leu Asn Gly Leu Tyr Pro Glu Ala Cys Asp
        50                  55                  60

Gly Ile Gln Ser Gly His Val Phe Leu Phe Gln Lys Pro Val Thr Asp
65                  70                  75                  80

Ala Glu Thr Ser Glu Thr Ile Thr Gln His Ala Gly Val Val Phe Gln
```

85                  90                  95
Asp Pro Asp Gln Gln Phe Cys Met Leu Thr Val Glu Asp Glu Ile Ala
            100                 105                 110
Phe Gly Leu Glu Asn Leu Gln Ile Pro Lys Glu Glu Met Thr Glu Lys
            115                 120                 125
Ile Asn Ala Val Leu Gly Lys Leu Arg Ile Thr His Leu Lys Glu Lys
            130                 135                 140
Met Ile Ser Thr Leu Ser Gly Gly Gln Lys Gln Lys Val Ala Leu Ala
145                 150                 155                 160
Cys Ile Leu Ala Met Glu Pro Glu Leu Ile Leu Asp Glu Pro Thr
                    165                 170                 175
Ser Leu Leu Asn Pro Phe Ser Ala Arg Glu Phe Val His Leu Met Lys
                    180                 185                 190
Asp Leu Gln Arg Glu Lys Gly Phe Ser Leu Leu Val Ile Glu His Gln
            195                 200                 205
Leu Asp Glu Trp Ala Pro Trp Ile Glu Arg Thr Ile Val Leu Asp Lys
210                 215                 220
Ser Gly Lys Lys Ala Leu Asp Gly Leu Thr Lys Asn Leu Phe Gln His
225                 230                 235                 240
Glu Ala Glu Thr Leu Lys Lys Leu Gly Ile Ala Ile Pro Lys Val Cys
            245                 250                 255
His Leu Gln Glu Lys Leu Ser Met Pro Phe Thr Leu Ser Lys Glu Met
            260                 265                 270
Leu Phe Lys Glu Pro Ile Pro Ala Gly His Val Lys Lys Lys Ala
            275                 280                 285
Pro Ser Gly Glu Ser Val Leu Glu Val Ser Ser Leu Ser Phe Ala Arg
            290                 295                 300
Gly Gln Gln Ala Ile Phe Lys Asp Ile Ser Phe Ser Leu Arg Glu Gly
305                 310                 315                 320
Ser Leu Thr Ala Leu Val Gly Pro Asn Gly Thr Gly Lys Ser Thr Leu
                    325                 330                 335
Leu Ser Val Leu Ala Ser Leu Met Lys Pro Gln Ser Gly Lys Ile Leu
            340                 345                 350
Leu Tyr Asp Gln Pro Leu Gln Lys Tyr Lys Glu Lys Glu Leu Arg Lys
            355                 360                 365
Arg Met Gly Phe Val Phe Gln Asn Pro Glu His Gln Phe Val Thr Asp
            370                 375                 380
Thr Val Tyr Asp Glu Leu Leu Phe Gly Gln Lys Ala Asn Ala Glu Thr
385                 390                 395                 400
Glu Lys Lys Ala Gln His Leu Leu Gln Arg Phe Gly Leu Ala His Leu
            405                 410                 415
Ala Asp His His Pro Phe Ala Ile Ser Gln Gly Gln Lys Arg Arg Leu
            420                 425                 430
Ser Val Ala Thr Met Leu Met His Asp Val Lys Val Leu Leu Leu Asp
            435                 440                 445
Glu Pro Thr Phe Gly Gln Asp Ala Arg Thr Ala Ala Glu Cys Met Glu
            450                 455                 460
Met Ile Gln Arg Ile Lys Ala Glu Gly Thr Ala Val Leu Met Ile Thr
465                 470                 475                 480
Gln Gly Tyr Gly Ala Ser Leu Phe Val Cys
            485                 490

<210> SEQ ID NO 38
<211> LENGTH: 490

```
<212> TYPE: PRT
<213> ORGANISM: Bacillus subtilis

<400> SEQUENCE: 38

Met Gln Ala Phe Asp Glu Leu Leu Thr Val Glu Gln Leu Ser Phe Ser
1               5                   10                  15

Tyr Glu Glu Asp Glu Lys Pro Val Phe Gln Asp Ile Ser Phe Glu Leu
            20                  25                  30

Gln Lys Gly Glu Cys Val Leu Leu Gly Pro Ser Gly Cys Gly Lys
        35                  40                  45

Ser Ser Leu Ala Leu Cys Leu Asn Gly Leu Tyr Pro Glu Ala Cys Asp
    50                  55                  60

Gly Ile Gln Ser Gly His Val Phe Leu Phe Gln Lys Pro Val Thr Asp
65                  70                  75                  80

Ala Glu Thr Ser Glu Thr Ile Thr Gln His Ala Gly Val Val Phe Gln
                85                  90                  95

Asp Pro Asp Gln Gln Phe Cys Met Leu Thr Val Glu Asp Glu Ile Ala
            100                 105                 110

Phe Gly Leu Glu Asn Leu Gln Ile Pro Lys Glu Glu Met Thr Glu Lys
        115                 120                 125

Ile Asn Ala Val Leu Gly Lys Leu Arg Ile Thr His Leu Lys Glu Lys
130                 135                 140

Met Ile Ser Thr Leu Ser Gly Gly Gln Lys Gln Lys Val Ala Leu Ala
145                 150                 155                 160

Cys Ile Leu Ala Met Glu Pro Glu Leu Ile Ile Leu Asp Glu Pro Thr
                165                 170                 175

Ser Leu Leu Asp Pro Phe Ser Ala Arg Glu Phe Val His Leu Met Lys
            180                 185                 190

Asp Leu Gln Arg Glu Lys Gly Phe Ser Leu Leu Val Ile Glu His Gln
        195                 200                 205

Leu Asp Glu Trp Ala Pro Trp Ile Glu Arg Thr Ile Val Leu Asp Lys
210                 215                 220

Ser Gly Lys Lys Ala Leu Asp Gly Leu Thr Lys Asn Leu Phe Gln His
225                 230                 235                 240

Glu Ala Glu Thr Leu Lys Lys Leu Gly Ile Ala Ile Pro Lys Val Cys
                245                 250                 255

His Leu Gln Glu Lys Leu Ser Met Pro Phe Thr Leu Ser Lys Glu Met
            260                 265                 270

Leu Phe Lys Glu Pro Ile Pro Ala Gly His Val Lys Lys Lys Ala
        275                 280                 285

Pro Ser Gly Glu Ser Val Leu Glu Val Ser Ser Leu Ser Phe Ala Arg
290                 295                 300

Gly Gln Gln Ala Ile Phe Lys Asp Ile Ser Phe Ser Leu Arg Glu Gly
305                 310                 315                 320

Ser Leu Thr Ala Leu Val Gly Pro Asn Gly Thr Gly Lys Ser Thr Leu
                325                 330                 335

Leu Ser Val Leu Ala Ser Leu Met Lys Pro Gln Ser Gly Lys Ile Leu
            340                 345                 350

Leu Tyr Asp Gln Pro Leu Gln Lys Tyr Lys Glu Lys Glu Leu Arg Lys
        355                 360                 365

Arg Met Gly Phe Val Phe Gln Asn Pro Glu His Gln Phe Val Thr Asp
370                 375                 380

Thr Val Tyr Asp Glu Leu Leu Phe Gly Gln Lys Ala Asn Ala Glu Thr
385                 390                 395                 400
```

-continued

| | | | | | | | | | | | | | |
|---|---|---|---|---|---|---|---|---|---|---|---|---|---|
| Glu | Lys | Lys | Ala | Gln | His | Leu | Leu | Gln | Arg | Phe | Gly | Leu | Ala | His | Leu |
| | | | | 405 | | | | 410 | | | | | 415 | | |
| Ala | Asp | His | His | Pro | Phe | Ala | Ile | Ser | Gln | Gly | Gln | Lys | Arg | Arg | Leu |
| | | | 420 | | | | | 425 | | | | | 430 | | |
| Ser | Val | Ala | Thr | Met | Leu | Met | His | Asp | Val | Lys | Val | Leu | Leu | Leu | Asp |
| | | 435 | | | | | 440 | | | | | 445 | | | |
| Glu | Pro | Thr | Phe | Gly | Gln | Asp | Ala | Arg | Thr | Ala | Ala | Glu | Cys | Met | Glu |
| | 450 | | | | | 455 | | | | | 460 | | | | |
| Met | Ile | Gln | Arg | Ile | Lys | Ala | Glu | Gly | Thr | Ala | Val | Leu | Met | Ile | Thr |
| 465 | | | | | 470 | | | | | 475 | | | | | 480 |
| Gln | Gly | Tyr | Gly | Ala | Ser | Leu | Phe | Val | Cys | | | | | | |
| | | | | 485 | | | | | 490 | | | | | | |